United States Patent
Gerber et al.

(10) Patent No.: US 12,162,995 B2
(45) Date of Patent: *Dec. 10, 2024

(54) HYDROGELS BASED ON FUNCTIONALIZED POLYSACCHARIDES

(71) Applicant: ECOLE POLYTECHNIQUE FEDERALE DE LAUSANNE (EPFL), Lausanne (CH)

(72) Inventors: Sandrine Gerber, Etoy (CH); Solene Passemard, Barcelona (ES); Christine Wandrey, Ecublens (CH); Leo Buhler, Cologny (CH); Philippe Morel, Vandoeuvres (CH)

(73) Assignee: ECOLE POLYTECHNIQUE FEDERALE DE LAUSANNE (EPFL), Lausanne (CH)

( * ) Notice: Subject to any disclaimer, the term of this patent is extended or adjusted under 35 U.S.C. 154(b) by 0 days.

This patent is subject to a terminal disclaimer.

(21) Appl. No.: 17/991,608

(22) Filed: Nov. 21, 2022

(65) Prior Publication Data

US 2023/0279186 A1  Sep. 7, 2023

Related U.S. Application Data

(63) Continuation of application No. 16/332,696, filed as application No. PCT/EP2017/073174 on Sep. 14, 2017, now Pat. No. 11,542,371.

(30) Foreign Application Priority Data

Sep. 14, 2016  (EP) ..................................... 16188771
Jul. 13, 2017  (EP) ..................................... 17181292

(51) Int. Cl.
*C08J 3/075* (2006.01)
*A61K 9/06* (2006.01)
*A61K 9/50* (2006.01)

(52) U.S. Cl.
CPC ................. *C08J 3/075* (2013.01); *A61K 9/06* (2013.01); *A61K 9/5036* (2013.01); *C08J 2305/04* (2013.01); *C08J 2471/02* (2013.01)

(58) Field of Classification Search
None
See application file for complete search history.

(56) References Cited

U.S. PATENT DOCUMENTS

2008/0305489 A1  12/2008  Thomas et al.
2015/0290327 A1  10/2015  Zenobi-Wong et al.
2020/0270402 A1   8/2020  Gerber et al.

FOREIGN PATENT DOCUMENTS

| EP | 1222926 A1 | 7/2002 |
| EP | 1806367 A2 | 7/2007 |
| JP | 201356955 A | 3/2013 |
| WO | 2006/116742 A2 | 11/2006 |
| WO | 2010/078036 A3 | 7/2010 |
| WO | 2012/167223 A1 | 12/2012 |
| WO | 2015/154078 A1 | 10/2015 |
| WO | 2016/073488 A1 | 5/2016 |

OTHER PUBLICATIONS

International Search Report issued in PCT/EP2017/073174 dated Jun. 12, 2017.
Written Opinion issued in PCT/EP2017/073174 dated Jun. 12, 2017.
Lee, K. Y., and Mooney, D. J., "Alginate: Properties and biomedical applications," Prog. Polym. Sci. 2012, 37, 106?126.
Goh, C. H., et al., "Alginates as a useful natural polymer for microencapsulation and therapeutic applications," Carbohydr. Polym. 2012, 88, 1?12.
Nedovic, V., and Willaert, R., "Applications of Cell Immobilization Biotechnology," Springer: Dordrecht, 2005.
O'Sullivan, E. S., et al., "Islets transplanted in immunoisolation devices: A review of the progress and the challenges that remain," Endocr. Rev. 2011, 32, 827?844.
Basta, G., and Calafiore, R., "Immunoisolation of pancreatic islet grafts with no recipient's immunosuppression: Actual and future perspectives," Curr. Diabetes Rep. 2011, 11, 384?391.
Drury, J. L., et al., "The tensile properties of alginate hydrogels," Biomaterials 2004, 25, 3187?3199.
Moya, M. L., et al., "Stability of alginate microbead properties in vitro," J. Mater. Sci.: Mater. Med. 2012, 23, 903?912.
King, A., et al., "Improvement of the biocompatibility of alginate/poly-L-lysine/alginate microcapsules by the use of epimerized alginate as a coating," J. Biomed. Mater. Res., Part A 2003, 64, 533?539.
Chen, A. Z., et al., "Molecular biocompatibility evaluation of poly-L-ornithine-coated alginate microcapsules by investigating mRNA expression of proinflammatory cytokines," J. Biomimetics Biomater. Tissue Eng. 2012, 14, 53?64.
Wandrey, C., et al., "Influence of alginate characteristics on the properties of multi-component microcapsules," J. Microencapsulation 2003, 20, 597?611.
Hu, X., et al., "Chemically crosslinked chitosan hydrogel loaded with gelatin for chondrocyte encapsulation," Biotechnol. J. 2011, 6, 1388-1396.
Fu, Y., et al., "3D cell entrapment in crosslinked thiolated gelatin-poly(ethylene glycol) diacrylate hydrogels," Biomaterials 2012, 33, 48-58.
Brunsen, A., et al., "Photocrosslinkable dextran hydrogel films as substrates for osteoblast and endothelial cell growth," J. Mater. Chem. 2012, 22, 19590-19604.
Bian, L., et al., "The influence of hyaluronic acid hydrogel crosslinking density and macromolecular diffusivity on human MSC chondrogenesis and hypertrophy," Biomaterials 2013, 34, 413-421.
Rockstad, A. M., et al., "The induction of cytokines by polycation containing microspheres by a complement dependent mechanism," Biomaterials 2013, 34, 621-630.
Vériter, S., et al., "In vivo selection of biocompatible alginates for islet encapsulation and subcutaneous transplantation," Tissue Eng.: Part A, 2010, 16, 1503-1513.

(Continued)

*Primary Examiner* — Layla D Berry
(74) *Attorney, Agent, or Firm* — Harness Dickey & Pierce P.L.C.

(57) ABSTRACT

The present invention relates to functionalized hydrogel networks grafted with at least one moiety for use in numerous fields, from cosmetics to surgery and medicine.

20 Claims, 8 Drawing Sheets

(56) References Cited

OTHER PUBLICATIONS

Dang, T. T., et al., "Enhanced function of immuno-isolated islets in diabetes therapy by co-encapsulation with an anti-inflammatory drug," Biomaterials 2013, 34, 5792-5801.

Mahou, R., and Wandrey, C., "Alginate-poly(ethylene glycol) hybrid microspheres with adjustable physical properties," Macromolecules 2010, 43, 1371-1378.

Mahou, R., et al., "Combined electrostatic and covalent polymer network for cell microencapsulation," Macromol. Symp. 2013, 329, 49-57.

Mahou, R., et al., "Tuning the Properties of Hydrogel Microspheres by Adding Chemical Crosslinking Functionality to Sodium Alginate," Chem. Mater. 2015, 27, 4380-4389.

Mahou, R., and Wandrey, C., "Versatile Route to Synthesize Heterobifunctional Poly(ethylene glycol) of Variable Functionality for Subsequent Pegylation," Polymers 2012, 4, 561-589.

Passemard, S., et al., "Convenient synthesis of bifunctional azido and amino-silanized poly(ethylene glycol) suitable for the functionalization of iron oxide nanoparticles for biomedical applications," Bioorg. Med. Chem. Lett. 2013, 23, 5006-5010.

Schleeh, T., et al., "Synthesis enhancements for generating highly soluble tetrabutylammonium alginates in organic solvents," Carbohydr. Polym. 2014, 114, 493-499.

Mironi-Harpaz. I., et al., "Photopolymerization of cell-encapsulating hydrogels: crosslinking efficiency versus cytotoxicity," Acta Biomater. 2012, 8, 1838-1848.

Restriction Requirement issued in corresponding U.S. Appl. No. 16/332,696 dated Dec. 14, 2020.

Office Action issued in corresponding U.S. Appl. No. 16/332,696 dated Oct. 29, 2021.

Office Action issued in corresponding U.S. Appl. No. 16/332,696 dated Mar. 23, 2022.

Notice of Allowance issued in corresponding U.S. Appl. No. 16/332,696 dated May 9, 2022.

Notice of Allowance issued in corresponding U.S. Appl. No. 16/332,696 dated Sep. 8, 2022.

U.S. Appl. No. 16/332,696, filed Mar. 12, 2019.

HYDROGELS BASED ON FUNCTIONALIZED POLYSACCHARIDES

CROSS REFERENCE TO RELATED APPLICATIONS

This application is continuation of U.S. patent application Ser. No. 16/332,696 filed on 12 Mar. 2019, which is a national stage application under 35 U.S.C. § 371 of PCT International Application No. PCT/EP2017/073174, which has an international filing date of 14 Sep. 2017 and claims priority under 35 U.S.C. § 119 to European Patent Application No. 17181292.8 filed on 13 Jul. 2017 and to European Patent Application No. 16188771.6 filed on 14 Sep. 2016. The contents of each application recited above are incorporated herein by reference in their entirety.

FIELD OF THE INVENTION

The present invention relates to a functionalized hydrogel network grafted with at least one moiety for use in numerous fields, from cosmetics to surgery and medicine.

BACKGROUND OF THE INVENTION

The increasing incidence of age-related diseases and the limited availability of human donor material to replace dysfunctional cells and damaged tissues in patients have prompted the search for alternative transplantation therapies. Hydrogels, presenting a three dimensional (3D) structure, can serve as scaffolds for tissue engineering and as carrier for cells and drug delivery. The allo-/xeno-transplantation of encapsulated cells/tissues prevents adverse immunological response while allowing the crossing of oxygen, nutrients and secreted factors. In addition, cell microencapsulation offers protection against mechanical stress or deteriorating environmental effects. The water-soluble biopolymer sodium alginate (Na-alg) spontaneously forms hydrogels in the presence of some divalent cations, under mild conditions of pH and temperature [1, 2]. In particular, the hydrogel calcium alginate (Ca-alg) presents favorable properties for several biological and medical applications, including cell immobilization [3]. Despite the highly promising studies that have been directed toward the development of hydrogel microcapsules for the treatment of human diseases, routine clinical application of cell containing microcapsules still remains a challenge. Many requirements are imposed on the microcapsule materials: biocompatibility with both the host tissue and the enclosed cells, long-term stability of the mechanical strength and elasticity, maintenance of a favorable environment for cell survival and metabolic functionality, reproducible manufacturing protocols.

Alginate-based microspheres (MS) prepared by ionic cross-linking with divalent cations present, for some applications, insufficient mechanical properties and stability as well as defects in permselectivity [4-7]. To overcome these issues, many efforts were devoted to the improvement of Ca-alg MS or the replacement of Ca-alg by other materials. Representative developments in this field include the coating of Ca-alg MS with polycations such as poly (L-lysine) [8], poly(L-ornithine) [9] or poly(methylene guanidine) [10] and their derivatives, and the use of other polymers such as chitosan [11], poly(ethylene glycol) (PEG) [12], dextran [13] and hyaluronic acid [14].

However, these modifications often led to reduced biocompatibility and implied complex multistep MS formation procedures [15]. For example, hydrogels were prepared from PEG diacrylate and dextran by photopolymerisation in presence of long-wave ultraviolet light activated photoinitiators (WO 2010/078036). Such procedure requires optimization of the type of photoinitiators, their concentration, and the UV light intensity to achieve maximal mechanical properties of the hydrogel. Cytocompatibility may be compromised by prolonged exposure to cytotoxic free radicals leading to reactions of cytotoxicity to encapsulated cells [25]. In addition, dextran based hydrogels cannot be envisaged for long-term treatment as they deteriorate rapidly allowing the release by diffusion of the encapsulated compound. Furthermore, inflammatory reactions were observed in presence of dextran-based hydrogels.

Other modifications of polymeric hydrogels involve the incorporation of bioactive molecules to improve the viability and functionality of encapsulated cells, and release therapeutic payloads at the site of transplantation. Small peptide sequences have been coupled to alginate molecules to improve cell spreading and growth in the microcapsules but resulted in high degree of degradation and fibrosis in vivo [16].

Another approach consists in the co-encapsulation of selected drugs and cells of interest within hydrogel microcapsules to reduce adverse fibrotic overgrowth at the site of implantation. In particular, the co-encapsulation of rat islets and curcumin in alginate hydrogels resulted in improved glycemic control and reduced pericapsular overgrowth in vivo [17]. An alternative promising approach proposes the design of hydrogel MS combining the fast ionotropic gelation of alginate with covalent cross-linking resulting from PEG derivatives, either covalently linked to the alginate backbone or in the form of an interpenetrating network. Following this concept, two types of two-component MS were recently developed, composed of Ca-alg and interpenetrating covalently cross-linked networks formed from vinyl sulfone-terminated multiarm PEG [18-20] or Na-alg functionalized with cysteamine [21], which showed favorable properties for cell microencapsulation. In addition, one-component MS resulting from ionotropic gelation and simultaneous covalent cross-linking interactions of PEG-grafted alginates were produced and demonstrated improved mechanical properties and permeability compared to pure Ca-alg MS [21].

Nevertheless, lack of in vivo stability of the MS in immunocompetent mice models asked for the design of new grafting methodologies for the conjugation of thiol-terminated PEG derivatives to the hydroxyl functionalities of the alginate backbone in order to produce stable biocompatible MS with no adverse effects following transplantation and no cytotoxicity to encapsulated cells, with potential for the local controlled delivery of anti-inflammatory agents.

LIST OF ABBREVIATIONS

Alg, alginate; Na-Alg, sodium alginate; Ca-Alg, calcium alginate; Boc, tert-butyloxycarbonyl; CDI, carbodiimidazole; DMF, N,N-dimethyl formamide; DMSO, dimethyl sulfoxide; EDCI, 1-ethyl-3-[3-(dimethylamino)propyl]carbodiimide; FITC, fluorescein isothiocyanate; hr, hour; MOPS, 3-(N-morpholino) ethanesulfonic acid; MS, microsphere; MWCO, molecular weight cut-off; NHS, N-hydroxysuccinimide; PE, petroleum ether; PEG, poly(ethylene glycol); rt, room temperature; TBA, tert-butyl ammonium; TCEP, tris(2-carboxyethyl)phosphine; Ts, tosylate;

SUMMARY OF THE INVENTION

The present invention relates to functionalized hydrogel networks based on polysaccharide grafted with at least one moiety wherein the hydrogel is an anionic polysaccharide and the moiety is a synthetic biocompatible polymer grafted on at least one hydroxyl group of said anionic polysaccharide.

Another aspect of the present invention concerns a composition comprising a functionalized hydrogel of the invention combined with at least one second element selected among cells, proteins, nucleic acids or other molecules.

A further aspect of the invention concerns a pharmaceutical composition comprising a composition of the invention and a pharmaceutically acceptable carrier.

Another aspect concerns a process for preparing a functionalized hydrogel network, the process comprising reacting an anionic polysaccharide with a moiety functionalized to allow the formation of a covalent bond between the polysaccharide and the moiety on one hydroxyl group of the polysaccharide.

Another aspect concerns a process for preparing a functionalized alginate based hydrogel, the process comprising
  i) converting one or more carboxylic acid functional groups of alginate or one or more carboxylate functional groups of alginate salt into TBA carboxylates,
  ii) modifying one or more hydroxyl groups of said alginate, or salt thereof, by reacting one or more hydroxyl groups in the presence of carbodiimidazole followed by precipitation,
  iii) preparing thiol-functionalized PEG derivatives (PEG I, PEG II and PEG III) by
    iii1) reacting the intermediates α-amino-ω-azido poly(ethylene glycol) with protected 3-mercaptopropanoïc acid, followed by simultaneous reduction of the azido group and deprotection of the thiol functionality, to produce PEG I, or
    iii2) conjugating intermediates α-amino-ω-azido poly(ethylene glycol) to activated lipoic acid followed by reduction in the presence of LiAlH4 so as to deliver PEG II as mixtures of opened (reduced) and closed (oxidized) forms of the lipoyl functionality, or
    iii3) contacting intermediates α-amino-ω-azido poly(ethylene glycol) 1a and 1b with a triazole moiety using a click reaction catalyzed by copper species to produce PEG III,
  iv) grafting the modified alginate with PEG I, PEG II and/or PEG III to allow the formation of a covalent bond between the functionalized alginate and PEG I, PEG II and/or PEG III on one or more hydroxyl groups of said alginate or salt thereof,
  v) purifying alginate grafted to PEG through dialysis and freeze drying.

Another aspect concerns a method of treating a disease or disorder in a human or animal patient, comprising: implanting or transplanting into a human or animal patient a material selected among cells, proteins, nucleic acids or other molecules immobilized or microencapsulated in a functionalized hydrogel of the invention.

A further aspect concerns heterobifunctional PEG, or derivatives thereof, of formula I, II and/or III:

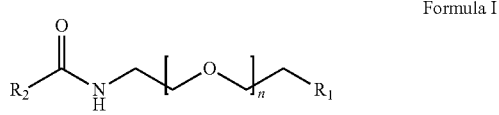

Formula I

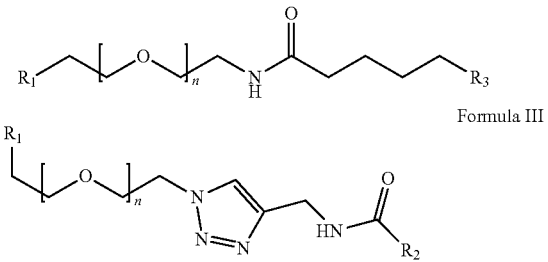

Formula II

Formula III wherein
n=8 to 50;
$R_1$ is independently selected from $NH_2$, $N_3$, OH, $C_{1-6}$ alkyl-$CO_2H$
$R_2$ is independently selected from $(CH_2)_pSH$, with p=2 to 10,

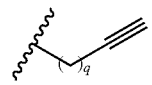

with q=2 to 5, and

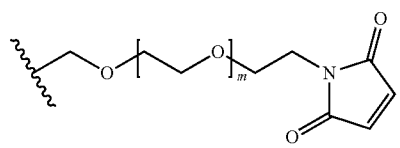

with m=2 to 10; $R_3$ is independently selected from

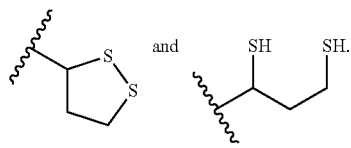

BRIEF DESCRIPTION OF THE FIGURES

FIG. 2A: Comparison of Alg-PEG-a I (3 wt %) and Alg-PEG-b I (4 wt %); FIG. 2B: Comparison of Alg-PEG-a II (3 wt %) and Alg-PEG-b II (4 wt %); FIG. 2C: Comparison of Alg-PEG-a I (3 wt %) and Alg-PEG-a II (3 wt %) and Alg-PEG-a III (3 wt %).; FIG. 2D: Comparison of Alg-PEG-a I (3 wt %) from TBA-Alg(x) and Alg-PEG-a I (2 wt %) from TBA-Alg(y), FIG. 2E: Comparison of Alg-PEG-a I, Alg-PEG-a II and Na-Alg (all formulations at 3 wt %); FIG. 2F: Comparison of Alg-PEG-b I, Alg-PEG-b II and Na-Alg (all formulations at 4 wt %).

FIG. 4A: photographs are from days 3 and 10 after microencapsulation and culture. Upper panels, light microscopy; middle panel, staining of live cells with fluorescein diacetate; lower panel, staining of dead cells with propidium iodide. For MS from AIG-PEG-a II, the decomposition of the capsular material over time is illustrated in the panel at the bottom. FIG. 4B: Cell viability measured at day 3, day 10 and day 15. Staining with fluorescein diacetate (FDA) of living cells and Propidium iodide (PI) for dead cells.

DESCRIPTION OF THE INVENTION

Figure 1:
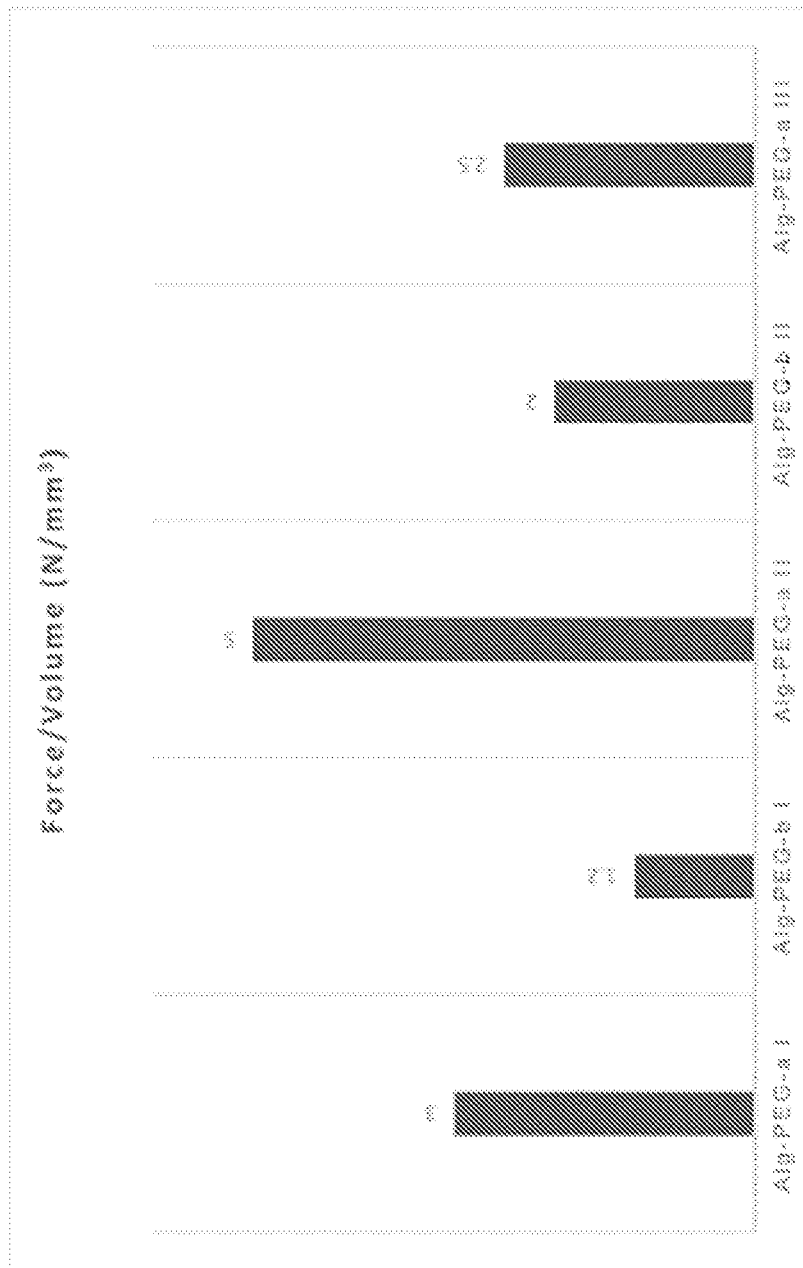
FIG. 1. Mechanical resistance to uniaxial compression to 90% of the initial MS diameter. All MS were prepared with PEG grafted alginates resulting from TBA-Alg(x).
Figure 2A:
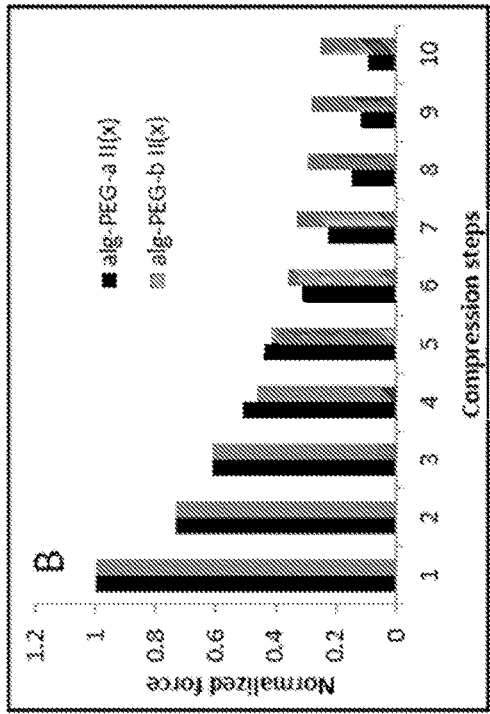
FIGS. 2A-2F. Resistance of the MS to 10 successive compressions.
Figure 2B:
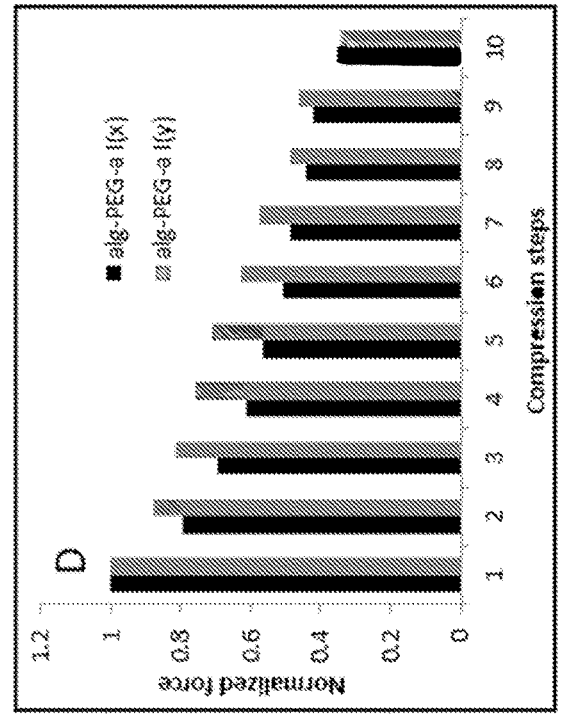
Figure 2C:
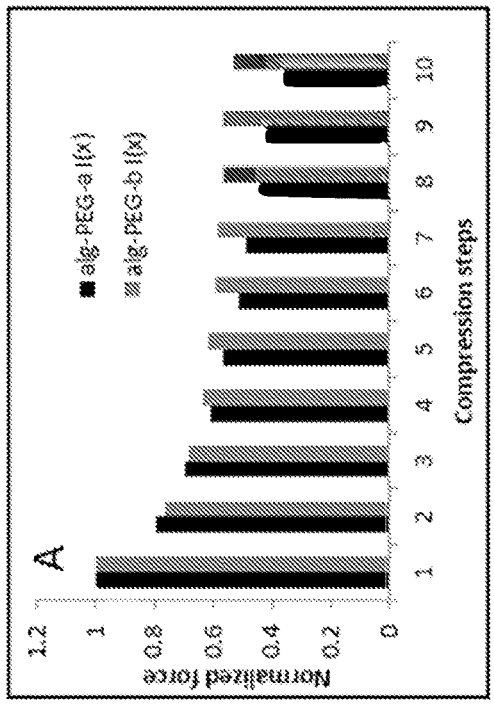
Figure 2D:
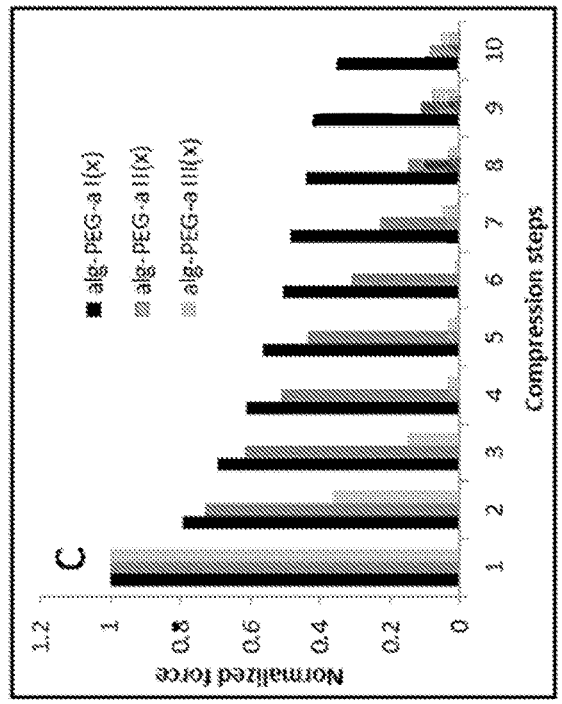
Figure 2E:
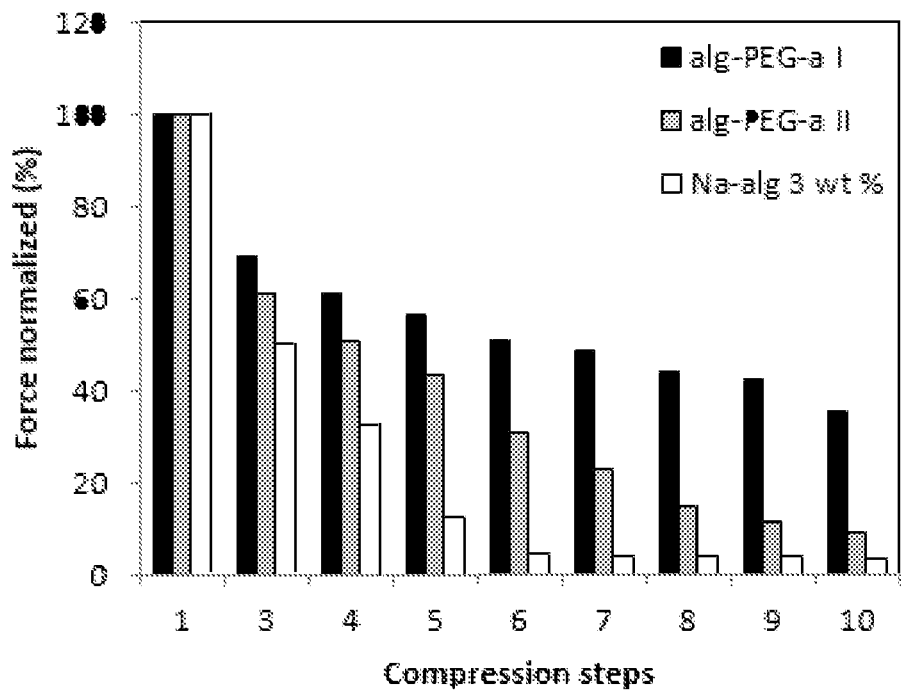
Figure 2F:
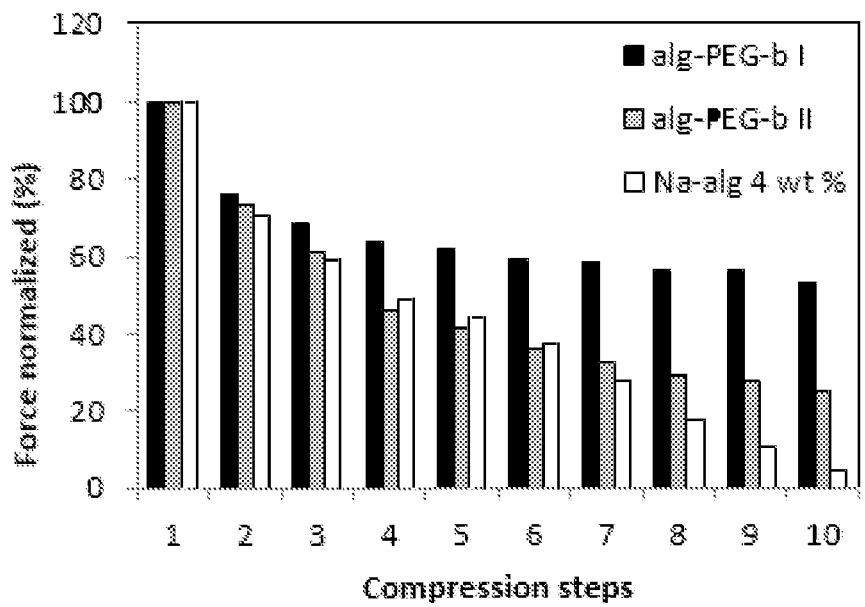

The methodology herein reported aims at the production of functionalized hydrogel networks grafted with at least one moiety, in the form of microspheres for different applications including cell therapy, addressing the following issues: tunable in vivo stability (i.e. mechanical, physical and chemical integrity), minimal side effects after transplantation, host and cell acceptance, tunable permeability and retrievability of the MS.

It must be noted that, as used in this specification and the appended claims, the singular forms "a," "an" and "the" include plural referents unless the content clearly dictates otherwise.

The present invention relates to a functionalized hydrogel grafted with at least one moiety, wherein the polymer is an anionic polysaccharide and the moiety is grafted on at least one hydroxyl group of said anionic polysaccharide.

Preferably, the polysaccharide is an anionic polysaccharide selected from the group comprising dextran, alginate, hyaluronan and galacturonan, a derivative of said polysaccharide or a salt thereof. It can be natural, synthetic or modified. Also envisioned is a combination of two or more anionic polysaccharides, e.g. alginate and hyaluronan.

Preferred anionic polysaccharide derivatives or modified anionic polysaccharide are polysaccharide ethers and polysaccharide esters. They can have one or more substituents, preferably of the types: hydroxyethyl, hydroxypropyl, hydroxybutyl, methyl, ethyl, propyl, dihydroxypropyl, carboxymethyl, sulfoethyl, hydrophobic long-chain branched and unbranched alkyl groups, hydrophobic long-chain branched and unbranched aryl groups or aryl alkyl groups, acetate, propionate, butyrate, lactate, nitrate or sulfate, of which some groups, such as, for example, hydroxyethyl, hydroxypropyl, hydroxybutyl, dihydroxypropyl and lactate, are capable of forming grafts. Alternatively, the anionic polysaccharide derivatives or modified anionic polysaccharides can be selected among those described in WO2012167223 which is incorporated herein by reference in its entirety. The substituents of the polysaccharides according to the invention are not limited to these groups.

The preferred salts of anionic polysaccharides according to the invention, are selected among the mono- or di-valent salts such as sodium, potassium, magnesium, calcium, strontium, barium, manganese salts. Sodium salts are most particularly preferred.

Most preferably, the anionic polysaccharide is alginate, a derivative thereof, or a salt thereof. Even more preferably, the anionic polysaccharide is sodium-alginate (Na-alginate or Na-alg).

The presence of the hydroxyl groups allows the polysaccharide to interact with the aqueous environment and to participate in hydrogen bonding, both within and between chains. In accordance with the present invention, a moiety is grafted on at least one hydroxyl group of said anionic polysaccharide.

According to the present invention, "grafted" means a covalent link between the anionic polysaccharide and the moiety. Preferably, the moiety is grafted to the anionic polysaccharide through an amide bond or an ether bond.

Alternatively, the moiety is grafted to the anionic polysaccharide through a spacer moiety between the anionic polysaccharide and the moiety. The spacer moiety may be selected among alkylenyl groups, cycloalkylenyl groups, alkenylenyl groups, eventually substituted by one or more substituents. Both the anionic polysaccharide and the moiety may be linked to the spacer on the same carbon atom, or on different carbon atoms.

For the requirements of the present invention, and as indicated herein in the description and claims, the term "functionalized hydrogel" or "functionalized hydrogel network" is understood to mean the necessary presence on the anionic polysaccharide of at least one carboxylate group or carboxylic acid functional group per saccharide monomeric unit. Preferably, there are 1 to 40, more preferably 5 to 40, most preferably 5 to 30 mol % modified hydroxyl groups on the polysaccharide backbone.

The moiety is preferably grafted on one hydroxyl group of said anionic poly-saccharide preferably through a carbamate bond or a carbonate bond.

The moiety can be any molecule or compound. Usually, the moiety is a synthetic biocompatible polymer, optionally comprising a therapeutic molecule.

Thus, the invention also relates to a functionalized hydrogel based on an anionic polysaccharide grafted with at least one moiety wherein the moiety is a synthetic biocompatible polymer grafted on at least one hydroxyl group of said anionic polysaccharide.

As used herewith, the term "biocompatible" refers to a polymer being not toxic, not injurious, nor physiologically reactive (e.g. no inflammation signs) and not causing immunological rejection in vivo.

Preferably, the synthetic biocompatible polymer is selected from the group comprising linear polyethylene glycol (PEG) (400 to 10'000 g·mol$^{-1}$), multi-arm PEG (4-arm or 8-arm, 3000 to 20'000 g·mol$^{-1}$), derivatives of linear and multi-arm PEG presenting terminal reactive functionalities (e.g. amine, azide, carboxylic acid, vinyl sulfone, acrylates, maleimide, thiol, dithiolane, alkyne, hydrazine, acyl hydrazine), Polyethylenimine, or a derivative of one or more of these polymers. Preferably, the therapeutic molecule is conjugated by covalent linkage, including ester, amide, sulfur-carbon bond, triazole.

Preferably also, the moiety is selected from the group comprising a Polyethylene Glycol (PEG), or a derivative thereof, and a therapeutic molecule.

In case the moiety is a PEG, or a derivative thereof, then said PEG, or derivative thereof, is a heterobifunctional PEG of formula I, II and/or III.

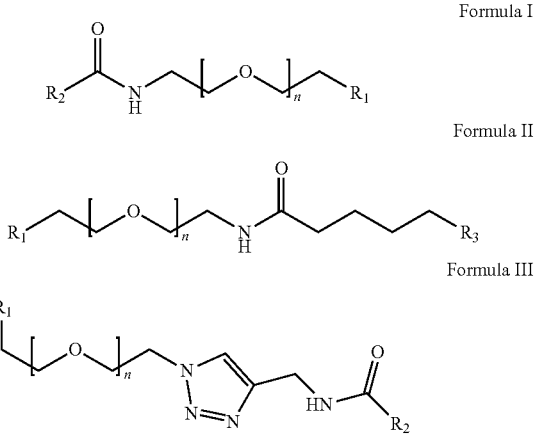

Formula I

Formula II

Formula III wherein
n=8 to 50, more preferably n=15 to 45, even more preferably n=20 to 44 and even more preferably n=22, 23, 24, 25, 26, 27, 28, 29, 30, 31, 32, 33, 34, 35, 36, 37, 38, 38, 39, 40, 41, 42, 43 or 44;
$R_1$ is independently selected from $NH_2$, $N_3$, OH, $C_{1-6}$ alkyl-$CO_2H$;
$R_2$ is independently selected from
$(CH_2)_p SH$, with p=2 to 10,

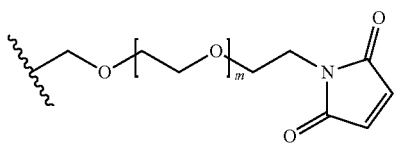

with q=2 to 5

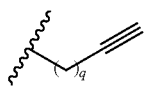

with m=2 to 10, preferably m=2 to 8, even more preferably m=3 to 8 and even more preferably n=3, 4, 5, 6, 7, or 8; $R_3$ is independently selected from

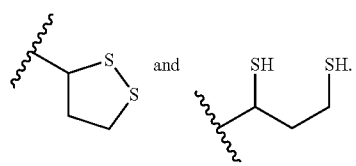 [SMILES: *C1CCSS1 ; *C(S)CCS]

Preferably, the $C_{1-6}$ alkyl-$CO_2H$ is $CH_2CO_2H$.

In accordance with the present invention, the PEG, or derivative thereof, is a heterobifunctional PEG derived from linear poly(ethylene glycol) $HOCH_2(CH_2OCH_2)_n CH_2OH$ with an average value of about 22 (PEG-a) or about 44 (PEG-b). Preferably, the heterobifunctional PEG is selected from the group comprising

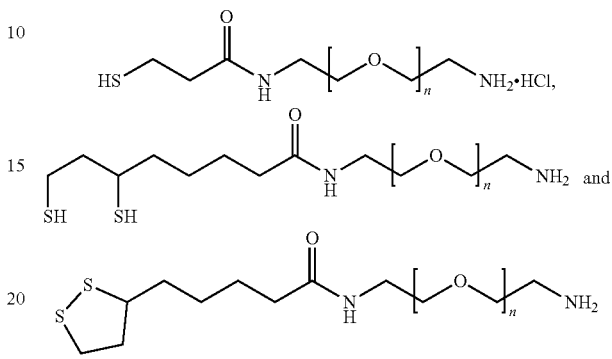

wherein n is comprised between 10 to 60, preferably between 20 to 50, and more preferably between 22 and 44.

The functionalized hydrogel of the invention is preferably in the form of a microsphere. Microspheres (MS) can be obtained by any techniques known in the art, such as for example spray-drying, emulsification-precipitation, water-in-oil emulsion solvent diffusion, emulsification-cross-linking methods and upon droplet extrusion into a gelation bath. Preferably, MS are obtained by extrusion into a gelation bath.

For example, microspheres of a functionalized hydrogel such Na-Alg-PEG polymers are prepared by dissolving said Na-Alg-PEG polymers in a solution of 0.4% NaCl in 100 mM MOPS buffer, pH 7.4 at the desired concentration. After complete dissolution, the polymer solution is directly extruded for gelification into a gelation bath (e.g. 100 mM $CaCl_2$) in 100 mM MOPS buffer, pH 7.4) containing tween 80 (1/10 000). The polymer solution, with or without cells, is extruded into the tenfold volume of the gelation bath containing $CaCl_2$ $2H_2O$ (100 mM) in MOPS. Microspheres are produced employing a coaxial air-flow droplet generator (such as for e.g. Encapsulator B-395 Pro, Büchi Labortechnik A G, Flawil, Switzerland). The microspheres are separated by filtration, washed twice with $CaCl_2$) stock solution, and finally stored in this solution at 4° C., or in cell culture medium in case of cell microencapsulation (Example 1).

In the present invention, MS are produced easily and in a short time (about few minutes) by simple extrusion into a gelation bath containing divalent cations leading to spontaneous formation of electronic and covalent interactions. Thus, the process by extrusion into a gelation bath has the advantage to use a one-component approach with no need for additional cross-linkers and photo-polymerization step (e.g. UV photo-crosslinking) which can be cytotoxic to cells for MS encapsulation.

As shown in the example 3, the MS diameters, after beads formation (day 1) and after one week (day 7), did not show significant changes indicating a good stability of the MS morphology (tables 2 and 3).

Furthermore, upon compression of 90% of their initial diameter, MS formed by Alg-PEG I and Alg-PEG II showed an increase of mechanical resistance (FIG. 1) and a good recovery performance after the 90% compression step (FIG. 2).

One aspect of the invention also concerns a composition comprising a functionalized hydrogel of the invention combined with at least a second element selected among cells, proteins, nucleic acids or other molecules. Preferably, the second element is encapsulated within the microspheres formed from the functionalized polymer by directly dispersing said second element in the polysaccharide solution before encapsulation.

The functionalized hydrogels of the invention can be used in numerous fields, from cosmetics to surgery and medicine. For example, they can be used, alone or combined with at least one second element, as films and membranes in various sectors of medicine, such as ophthalmology, dermatology, otorhinolaryngology, neurology, internal and cardiovascular surgery in particular as tissue substitutes and as agents to enable the adhesion of tissue surfaces (such as severed nerves) or in preventing surgical adherence, or for wound dressings.

The functionalized hydrogels of the invention can also be advantageously combined with cells from human, animal or vegetal origin, such as, e.g., keratinocytes, fibroblasts, osteocytes, chondrocytes, urocytes, stem cells, endothelial cells, pancreatic cells, liver cells and neural cells. Encapsulated cells can be transplanted into a patient in need thereof to treat a disease or disorder. In some aspects, the encapsulated cells are obtained from a genetically non-identical member of the same species or from genetically modified cells. In alternative aspects, the encapsulated cells are obtained from a different species than the patient. In preferred aspects, hormone- or protein-secreting cells are encapsulated and transplanted into a patient to treat a disease or disorder.

Figure 4:
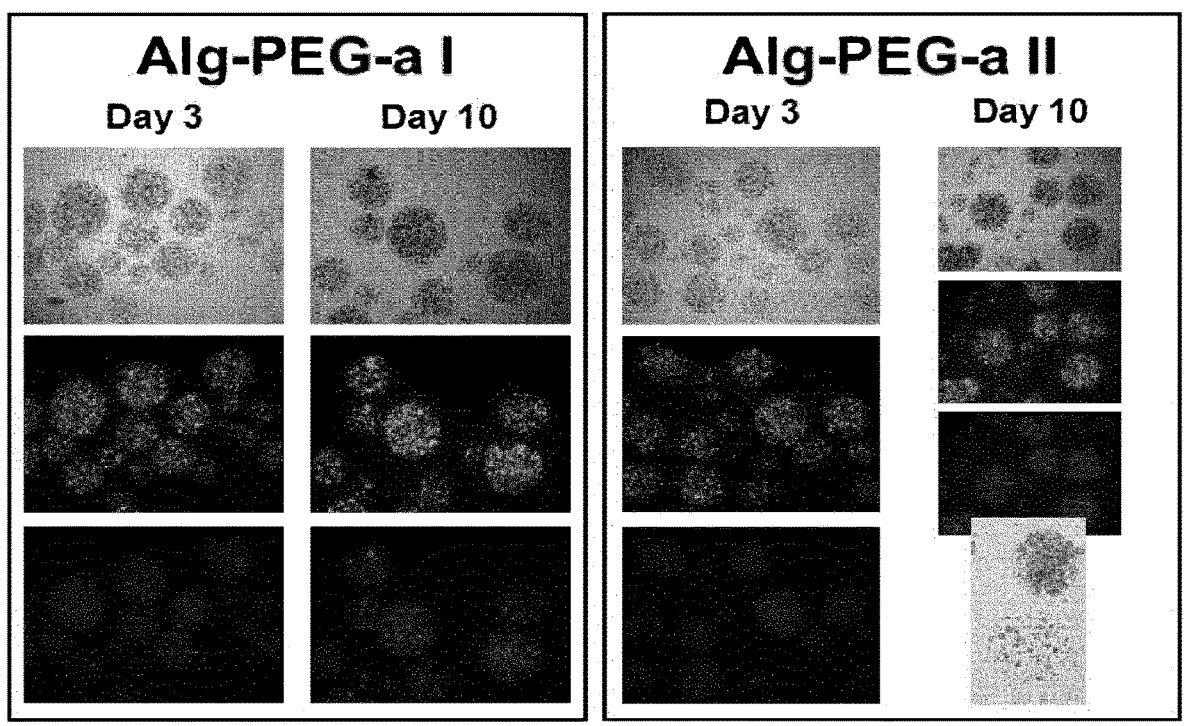
FIGS. 4A-4B. MIN6 cells microencapsulated in MS from Alg-PEG-a I and Alg-PEG-a II (average microsphere diameter: 500 µm).
Figure 4:
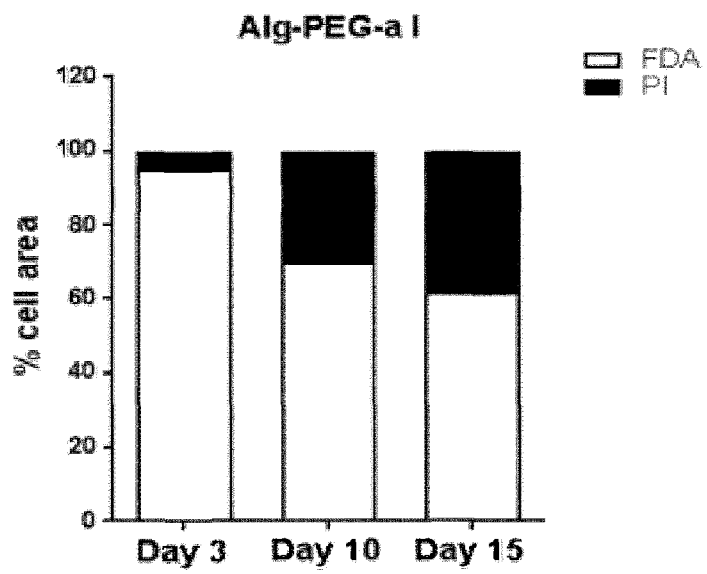
Figure 4:
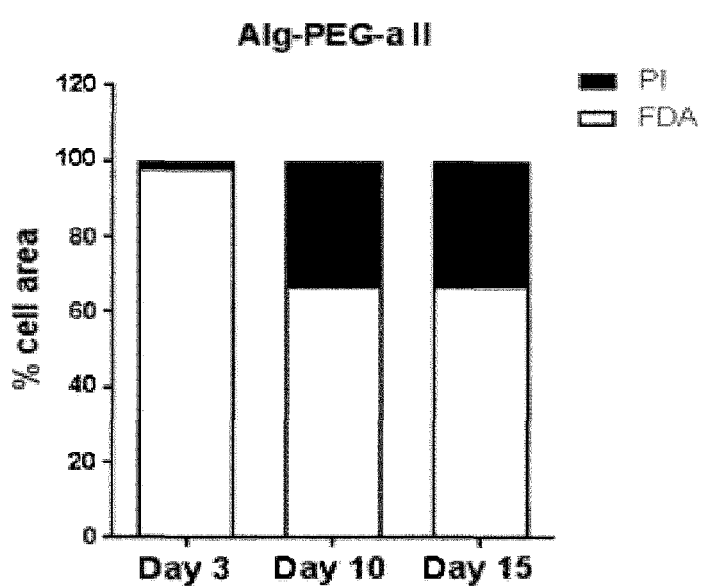

The MS of the present invention are compatible with a large variety of cells. For example, cell microencapsulation in MS was observed with cells of the mouse insulinoma cell line MIN6 (Example 4, FIG. 4) and with primary porcine hepatocytes (Example 6, FIGS. 6 and 7).

Furthermore, the MS of the present invention present advantageously different thiol-functionalized PEG grafting units (Scheme 2: Alg-PEG a I, Alg-PEG a II, Alg-PEG a III, Alg-PEG b I, and Alg-PEG b II) which can be selected for their different integrity over time or durability.

As shown in the example 4, the durability of the hydrogels depends on the nature of the covalent linkage provided by the thiol-functionalized PEG grafting units. The integrity of the MS from Alg-PEG a I system was confirmed up to day 15. In contrast, the integrity of the MS from Alg-PEG-a II system degraded over time and out-diffusion of the cells was observed around day 10. Thus, the thiol-functionalized PEG grafting unit influences the integrity of the microspheres network over time and the durability can be easily tuned by selecting the type of thiol-functionalized PEG grafting unit.

As used herewith, the "durability" refers to the physical and mechanical characteristics of the MS, notably morphology, size, and elasticity.

As used herewith, the "stability" refers to the chemical interactions involved in the MS network, in particular the electrostatic interactions and covalent crosslinking.

Figure 8:
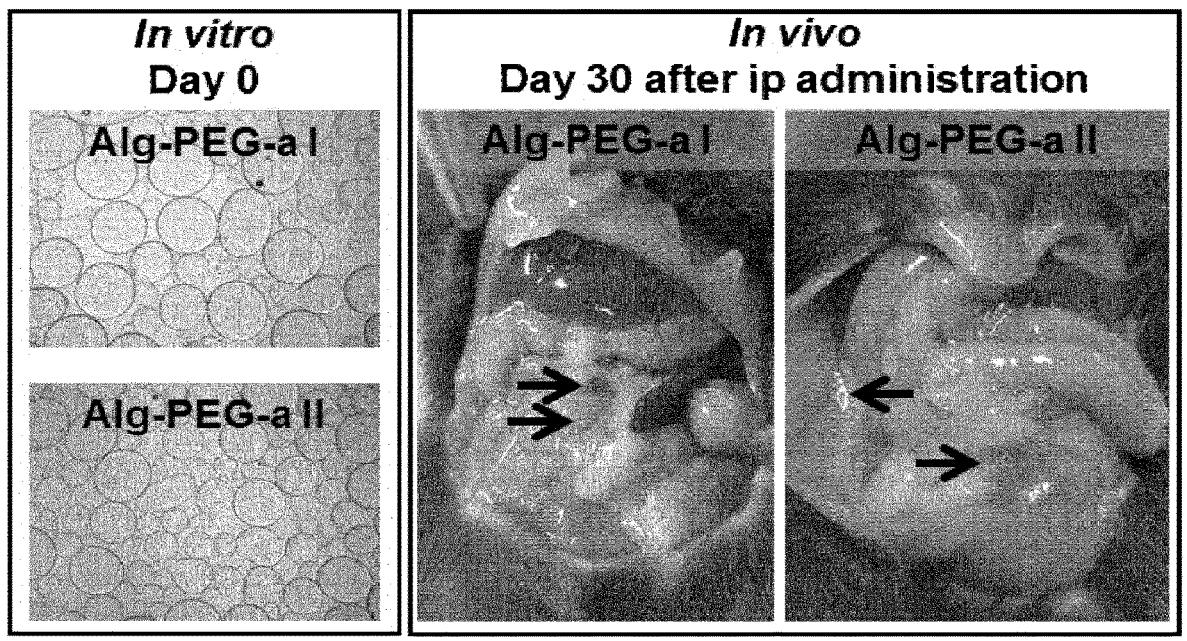
FIG. 8. Empty MS from Alg-PEG-a I and Alg-PEG-a II, directly after manufacture (microscopy, left panels), and at 30 days after intraperitoneal implantation in mice. Some MS are indicated by arrows.

Importantly, the MS of the present invention are biocompatible with no signs of inflammation. As shown in the example 7, the suitability of Alg-PEG-a I and Alg-PEG-a II systems for cell transplantation was assessed by transplantation of empty MS formed from both systems in immune-competent mice and there were no signs of inflammation, neither connective tissue formation nor fibrosis, indicating no major host incompatibility (FIG. 8).

Moreover as explained above, they can be advantageously utilized as coating for organs, such as cardiac valves, or blood vessels, or of biomedical articles such as urologic catheters. This type of coating improves to a high degree the biocompatibility of the article to be grafted, thereby improving the performance thereof at a biological level.

In particular, the functionalized hydrogels of the invention can be used as coating for blood vessels following coronary angioplasty, in repair following the dissection of blood vessels and the attachment of flaps on the walls of the same, following spontaneous detachment or lesion, and in the sealing of aneurisms.

In some aspects of the invention described herein, the functionalized hydrogel of the invention or a pharmaceutically acceptable salt thereof, is present in a pharmaceutical composition, along with at least one pharmaceutically acceptable carrier. Pharmaceutically acceptable carriers may include pharmaceutically adjuvants and/or other excipients, and other ingredients can be deemed pharmaceutically acceptable insofar as they are compatible with other ingredients of the formulation and not deleterious to the recipient thereof. The aim of the pharmaceutical composition of the invention is thus to provide functionalized hydrogels presenting the required properties for the stabilization, administration and delivery of a great diversity of active principles, and/or bioactive agents.

As used herewith, the term "drug" refers to a formulation which has been approved for therapeutic intervention.

As used herewith, the term "bioactive agent" refers to a molecule for which biological activity (on enzymes, cells, receptors . . . ) has been reported but has not been yet approved for therapeutic intervention.

As used herewith, the term "active principle" refers to a molecule which within a drug displays the therapeutic effect.

Depending on the condition being treated, the pharmaceutical composition can be formulated and administered systemically or locally. In one aspect, the present invention is targeted at providing functionalized polysaccharides, intended for the stabilization, administration and delivery of active principles, and/or bioactive agents, which can be prepared by methods which are relatively simple to employ and which offer an increased ability to be adjusted in terms of interaction properties. The aim of this aspect of the present invention is thus to provide functionalized polysaccharides presenting the required properties for the stabilization, administration and delivery of a great diversity of active principles, and/or bioactive agents.

The active principles, and/or bioactive agents of the pharmaceutical composition can be linked to the microspheres through non-covalent interactions (for example electrostatic interactions) and/or covalent interactions.

Thus, the kinetics of the release of the active principles, drugs and/or bioactive agents can be controlled over time depending on the nature of the interactions to the active principle, drugs and/or bioactive agent.

For example, the pharmaceutical composition reported herein can serve as carrier for the controlled delivery of molecular cargos (drugs, peptide sequences) after transplantation. Several anti-inflammatory agents (for instance, curcumin and ketoprofen) were derivatized for further conjugation to Alg-PEG microspheres, either by coupling to alginate hydroxyl moieties or covalent linking to the grafted PEG chains as shown below:

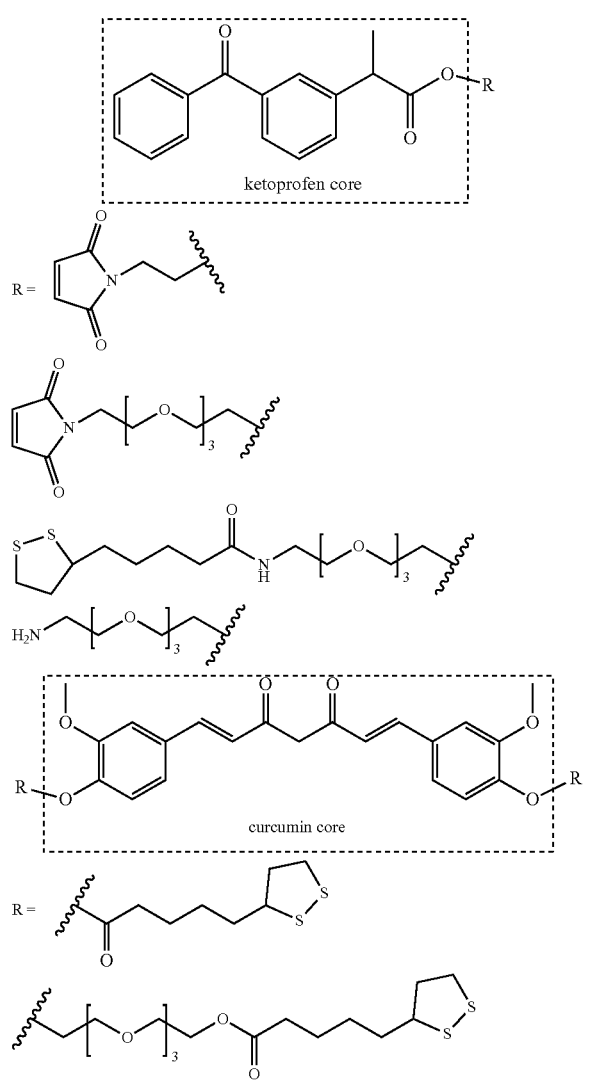

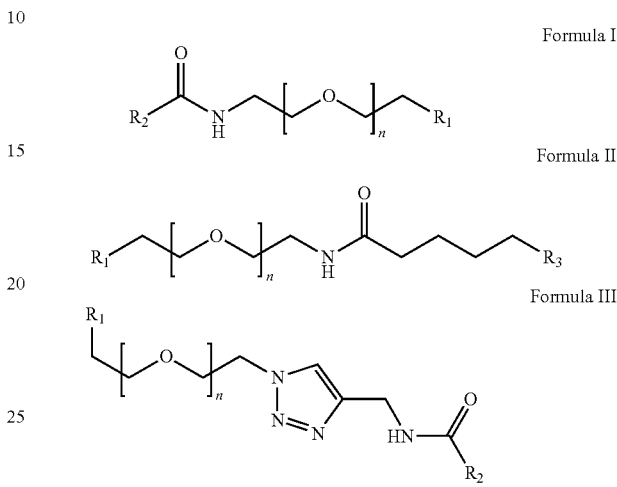

As shown in the example 8, Poly(ethylene glycol) derivatives functionalized were produced with the anti-inflammatory active principle ketoprofen (scheme 3), as well as MS showing a good stability (schemes 4 and 5). MS functionalized with ketoprofen were stable for 14 days.

Figure 9:
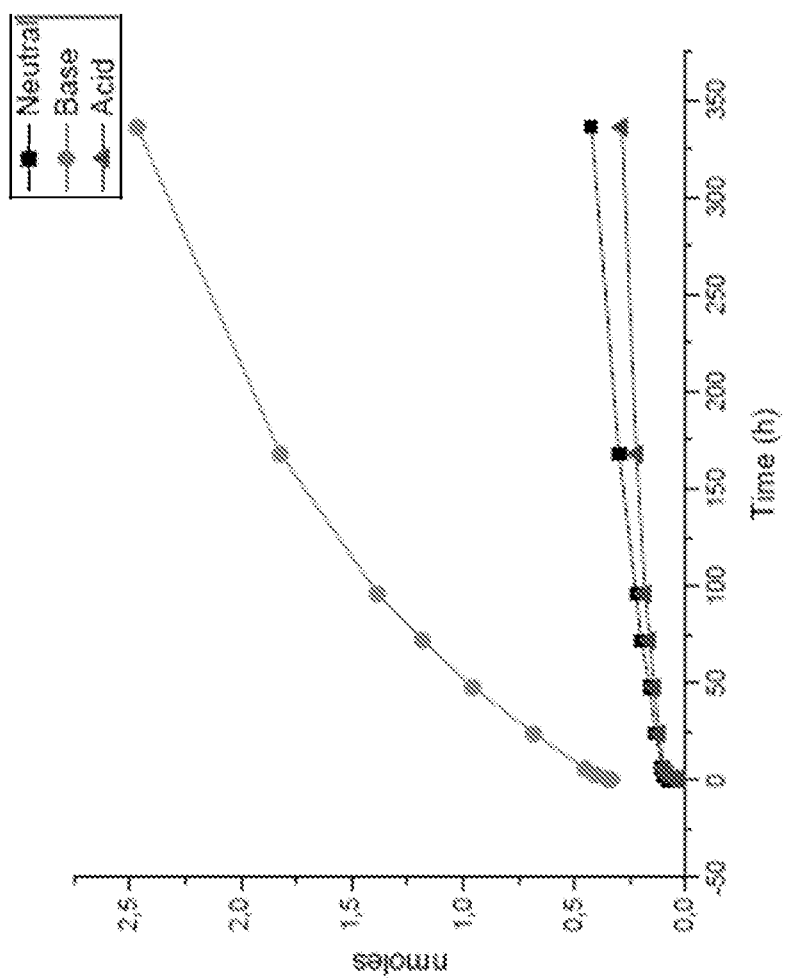
FIG. 9. Release of ketoprofen from MS quantified by LC-MS at pH 3, pH 7.4 and pH 11. The curves shows controlled release of ketoprofen over time.

Furthermore, the MS of the present invention as carrier present a controlled delivery of molecular cargos that can be modulated by selecting the pH. As shown in the example 8, a fast release of ketoprofen is observed at basic pH and slower releases are observed at physiological or acidic pH (FIG. 9).

Provided herein are also methods and processes for preparing functionalized hydrogels of the invention.

Typically, a process for preparing a functionalized hydrogel, comprises reacting an anionic polysaccharide with a moiety functionalized to allow the formation of a covalent bond between the polysaccharide and the moiety on at least one hydroxyl group of the polysaccharide.

Preferably, the polysaccharide is an anionic polysaccharide that comprises one or more carboxylic acid functional groups. This anionic polysaccharide is preferably selected from the group comprising dextran, alginate, hyaluronan and galacturonan, a derivative of said polysaccharide or a salt thereof. It can be natural, synthetic or modified. Also envisioned is a combination of two or more anionic polysaccharides, e.g. alginate and hyaluronan.

Usually, the moiety is selected from the group comprising a Polyethylene Glycol (PEG), or a derivative thereof, and a therapeutic molecule.

In case the moiety is a PEG, or a derivative thereof, then said PEG or a derivative thereof, is a heterobifunctional PEG of formula I, II and/or III.

wherein
n=8 to 50; more preferably n=15 to 45, even more preferably n=20 to 44 and even more preferably n=22, 23, 24, 25, 26, 27, 28, 29, 30, 31, 32, 33, 34, 35, 36, 37, 38, 38, 39, 40, 41, 42, 43 or 44;

$R_1$ is independently selected from $NH_2$, $N_3$, OH, $C_{1-6}$ alkyl-$CO_2H$;

$R_2$ is independently selected from:
$(CH_2)_p SH$, with p=2 to 10,

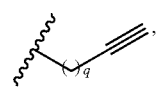

with q=2 to 5

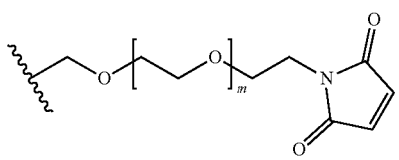

with m=2 to 10, more preferably m=2 to 8, even more preferably m=3 to 8 and even more preferably n=3, 4, 5, 6, 7, or 8;

$R_3$ is independently selected from

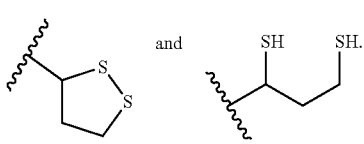 [SMILES: *C1CCSS1 ; *C(S)CCS]

Preferably, the $C_{1-6}$ alkyl-$CO_2H$ is $CH_2CO_2H$.

In accordance with the present invention, the PEG, or derivative thereof, is a heterobifunctional PEG derived from linear poly(ethylene glycol) $HOCH_2(CH_2OCH_2)_nCH_2OH$ with average n value of 22 (PEG-a) or 44 (PEG-b). Preferably, the heterobifunctional PEG is selected from the group comprising

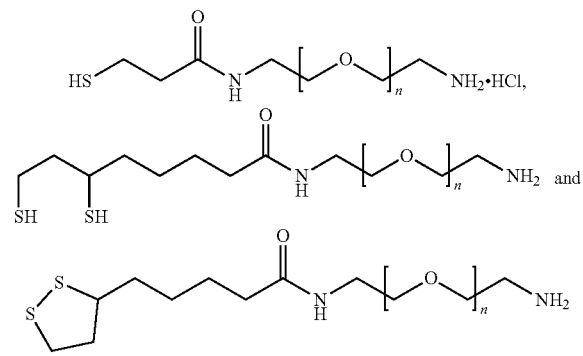

wherein n is comprised between 22 and 44.

A particular aspect of the present invention concerns a process for preparing a functionalized alginate based hydrogel, the process comprising
  i) converting one or more carboxylic acid functional groups of alginate or one or more carboxylate functional groups of alginate salt into TBA carboxylates,
  ii) modifying one or more hydroxyl groups of said alginate, or salt thereof, by reacting one or more hydroxyl groups in the presence of carbodiimidazole followed by precipitation,
  iii) preparing thiol-functionalized PEG derivatives (PEG I, PEG II and PEG III) by
    iii1) reacting the intermediates α-amino-ω-azido poly(ethylene glycol) with protected 3-mercaptopropanoïc acid, followed by simultaneous reduction of the azido group and deprotection of the thiol functionality, to produce PEG I, or
    iii2) conjugating intermediates α-amino-ω-azido poly(ethylene glycol) to activated lipoic acid followed by reduction in the presence of $LiAlH_4$ so as to deliver PEG II as mixtures of opened (reduced) and closed (oxidized) forms of the lipoyl functionality, or
    iii3) contacting intermediates α-amino-ω-azido poly(ethylene glycol) 1a and 1b with a triazole moiety using a click reaction catalyzed by copper species to produce PEG III,
  iv) grafting the functionalized alginate with PEG I, PEG II and/or PEG III to allow the formation of a covalent bond between the functionalized alginate and PEG I, PEG II and/or PEG III on one hydroxyl group of said alginate or salt thereof, and
  v) purifying the PEG-grafted alginate through dialysis and freeze drying.

The above process for preparing a functionalized alginate-based hydrogel was presented for the functionalization of the biopolymer sodium alginate with thiol containing poly(ethylene glycol) units. The first step of the synthetic pathway, which consists in heterogeneous acidification of Na-alg, can be adjusted to provide intermediates TBA-alg of different molar mass (Example 2, Scheme 2). From these intermediates, Alg-PEG derivatives are obtained by activation of hydroxyl moieties in the form of imidazolide, followed by formation of covalent carbamate linkage with heterocheletic PEG derivatives. TBA-alg intermediate of higher molecular mass led to more viscous solutions of the resulting Alg-PEG systems.

The combination of ionic gelation with divalent cations such as calcium ions Ca2+ or baryum Ba2+ and covalent self-cross-linking of the thiol moieties leads to MS presenting mechanical properties and permselectivity suitable for cell transplantation applications. Preferably, divalent cations are calcium ions.

As shown in the examples, fine-tuning of the MS properties, for example their durability and stability is obtained by variation on the PEG length and functionalities, degree of grafting and alg-PEG concentration. In addition, alginate chain degradation can be forced or avoided by slight modification of the grafting protocol.

The present invention also envisions a method of treating and/or preventing a disease or disorder in a human or animal patient, comprising: implanting or transplanting into a human or animal patient a material selected among cells, proteins, nucleic acids or other molecules encapsulated in a functionalized hydrogel of the invention.

In vitro and in vivo studies demonstrated the compatibility of functionalized hydrogels of the invention for cell microencapsulation and their potential for cell transplantation. Depending on the targeted applications, the properties of these functionalized hydrogel can be tuned to achieve long-term in vivo durability or degradation over time.

Also envisioned is a pharmaceutical composition for use in treating and/or preventing a disease or disorder in a human or animal patient, said pharmaceutical composition comprising a functionalized hydrogel of the invention combined with at least one second element selected among cells, proteins, nucleic acids or other molecules and a pharmaceutically acceptable carrier.

The present invention also relates to a method of treating and/or preventing a disease or disorder in a human or animal patient, comprising administering a pharmaceutical composition comprising a functionalized hydrogel of the invention combined with at least one second element selected among cells, proteins, nucleic acids or other molecules and a pharmaceutically acceptable carrier.

Another aspect also concerns the use of a functionalized hydrogel of the invention in the preparation of a medicament or drug or therapeutic product for the treatment and/or prevention of a disease or disorder in a human or animal patient.

The present invention also encompasses heterobifunctional PEG oligomers suitable for orthogonal functionalization on both ends of the polymers, or a derivative thereof, of formula I, II and/or III:

Formula I
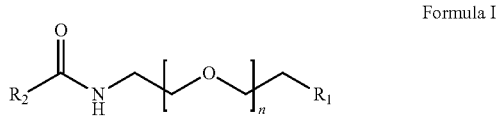

Formula II
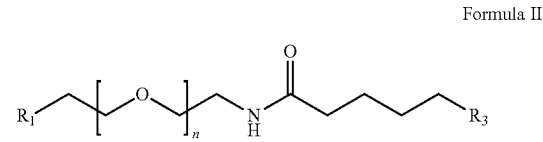

Formula III

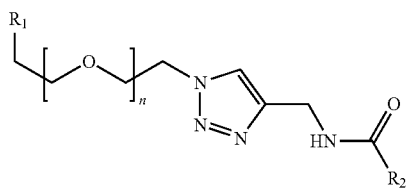

wherein n=8 to 50; more preferably n=15 to 45, even more preferably n=20 to 44 and even more preferably n=22, 23, 24, 25, 26, 27, 28, 29, 30, 31, 32, 33, 34, 35, 36, 37, 38, 38, 39, 40, 41, 42, 43 or 44;

$R_1$ is independently selected from $NH_2$, $N_3$, OH, $C_{1-6}$ alkyl-$CO_2H$;

$R_2$ is independently selected from $(CH_2)_p SH$, with p=2 to 10,

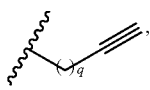

with q=2 to 5,

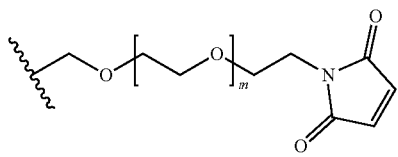

with m=2 to 10, more preferably m=2 to 8, even more preferably m=3 to 8 and even more preferably n=3, 4, 5, 6, 7, or 8;

$R_3$ is independently selected from

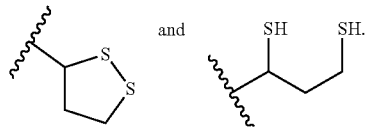 [SMILES: *C1CCSS1 ; *C(S)CCS]

Preferably, the $C_{1-6}$ alkyl-$CO_2H$ is $CH_2CO_2H$.

In accordance with the present invention, the PEG, or derivative thereof, is a heterobifunctional PEG derived from linear poly(ethylene glycol) $HOCH_2(CH_2OCH_2)_n CH_2OH$ with average n value of 22 (PEG-a) or 44 (PEG-b). Preferably, the heterobifunctional PEG is selected from the group comprising

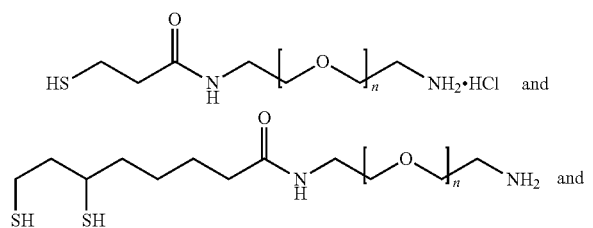

and

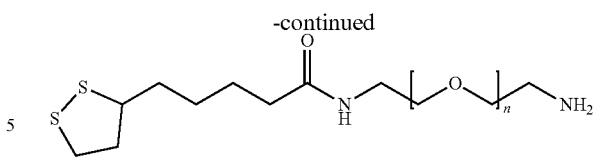

wherein n is comprised between 22 and 44.

EXAMPLES

1. Material & Methods

Chemical Syntheses—General Conditions

Na-alg Kelton HV (lot no. 61650A, [η]=813 mL g$^{-1}$ in 0.1 M NaCl, T=25° C., G/M=0.6) was obtained from Kelco (San Diego, USA, California). Linear PEGs (MM=1000 g·mol$^{-1}$ or 2000 g·mol$^{-1}$) were obtained from Sigma (Buchs, Switzerland). Other commercial reagents (Fluka, Sigma, Switzerland; TCI Europe, Zwijndrecht, Belgium) were used without further purification. Unless special mention, all reactions were performed under argon atmosphere (1 atm). Anhydrous solvents were obtained by filtration (Innovative Technology, Oldham, UK). Reactions were monitored by TLC (Merck silica gel 60F254 plates, Merck, Darmstadt, Germany). Detection was performed by UV light, $KMnO_4$, Ninhydrin or $I_2$. Purifications were performed by flash chromatography on silica gel (Merck N° 9385 silica gel 60, 240-400 mesh). IR spectra were recorded on a Perkin-Elmer-1420 spectrometer (Perkin-Elmer, Waltham, Massachusetts, USA). $^1$H-NMR spectra were recorded on a Bruker ARX-400 spectrometer (400 MHz) (Bruker, Billerica, Massachusetts, USA). $^{13}$C-NMR spectra were recorded on a Bruker ARX-400 spectrometer (100.6 MHz). Chemical shifts are expressed in parts per million (ppm) and coupling constants (J) in hertz. Solvents used for NMR spectroscopy are deuterated chloroform ($CDCl_3$, Acros) and deuterated methanol ($CD_3OD$, Acros). Mass spectra were obtained on a Nermag R-10-10C spectrometer with chemical ionization ($NH_3$) and mode m/z (amu) [% relative base peak (100%)] (Nermag, Santa Clara, California, USA).

Formation of One—Component Microspheres

Solutions of Na-Alg-PEG polymers were prepared according to the following formulation: Na-alg-PEG was dissolved in a solution of 0.4% NaCl in 100 mM MOPS buffer, pH 7.4 at the desired concentration. After full dissolution, the polymer solution was directly extruded for gelification into a gelation bath (100 mM $CaCl_2$) in 100 mM MOPS buffer, pH 7.4) containing tween 80 (¹⁄₁₀ 000). MS were produced employing a coaxial air-flow droplet generator (Encapsulator B-395 Pro, Büchi Labortechnik A G, Flawil, Switzerland). In case the polymer is used with cells, the polymer solution is sterilized by filtration. The polymer solution, with or without cells, was extruded into the tenfold volume of the gelation bath containing $CaCl_2 2H_2O$ (100 mM) in MOPS. The MS were collected by filtration, washed twice with $CaCl_2$) stock solution, and finally stored in this solution at 4° C., or in cell culture medium in case of cell microencapsulation.

Physical Characterization of Microspheres

The average diameter was measured on an Olympus AX70 microscope equipped with an Olympus DP70 color digital camera. The mechanical resistance to 90% compression of the initial MS diameter was analyzed using a texture analyzer (TA-XT2i, software Texture Exponent 32, Stable Micro Systems, Godalming, UK) equipped with a force transducer (1 mN resolution). A single MS was placed below the probe, for which a constant speed was set as 0.5 mm s$^{-1}$. Thirty MS of each batch were included in the analysis. The permeability of the MS was studied by measuring the ingress diffusion of FITC-dextran standards (40, 150 kg mol-1). Prior to the measurement, the MS were equilibrated in the gelation bath. 700 mg of MS, collected by filtration and gently dried on paper, were incubated in 1 mL of FITC-dextran solution (1 mg mL$^{-1}$ in 100 mM $CaCl_2$ solution). 40 µL of the supernatant were withdrawn after 1 min (t=0) and at defined time intervals, and diluted in 600 µL of the gelation bath. Fluorescence spectroscopy (Multiplate Reader Safire-II Tecan, Maennedorf, Switzerland) was used to monitor the FITC-dextran concentration.

Microencapsulation of MIN6 Cells

MIN6 cells were cultured in Dulbecco Modified Eagle's Medium (DMEM) supplemented with 1 mM Na-Pyruvate, 71 µM β-mercaptoethanol, 15% decomplemented Fetal Calf Serum, 25 mM glucose, penicillin and streptomycin (DMEM complete medium). 10×10$^6$ MIN6 cells were gently mixed in 1 mL of Na-alg-PEG solution. MS were produced using the same procedure as described above for the formation of one-component MS.

Encapsulated and free MIN6 cells were cultured up to 10 days or 15 days in DMEM complete medium and were analyzed for viability and functionality by FDA/PI staining and glucose-stimulated insulin release assay, as previously described (Meier R P, et al, PloS one, 2014).

Transplantation of MS in Mice

Animal research was performed according to the Geneva cantonal veterinary authorities (license GE/34/13). 1 mL of empty MS was transferred into the peritoneum of anesthetized immunocompetent C57/BL6 mice through a small abdominal incision. After 30 days, mice were sacrificed for a macroscopic evaluation of fibrotic reactions in the peritoneum.

2. Synthesis Protocols

Designation of the compounds refers to the chemical structures presented in Scheme 1 and Scheme 2.

A synthetic route was developed to functionalize the hydroxyl groups of the biopolymer sodium alginate with heterobifunctional PEG derivatives containing end thiol (I or III) or 1,2-dithiolane (II) functionalities for covalent cross-linking.

Preparation of Compound 2 (Scheme 1)

To a solution of 3-mercaptopropionic acid (1 equiv, 94.2 mmol, 10 g) in $H_2O$: THF (1:1, 180 mL) were added $Boc_2O$ (1.2 equiv, 113.04 mmol, 24.7 g) and $Et_3N$ (2 equiv, 188.4 mmol, 19.07 g, 25.43 mL) and the reaction mixture was stirred for 12 hr at rt. THF was evaporated under vacuo and 1 M HCl (50 mL) was added. The product was extracted with DCM (3×100 mL). The combined organic layers were dried ($MgSO_4$) and concentrated in vacuo. The product was purified by FCC on silica gel (PE/EtOAc 8:1) to afford 2 as a transparent oil (43.3 mmol, 8.92 g, 46%).

$^1$H-NMR (400 MHz, $CDCl_3$): δ 11.01 (s, $^1$H, COOH), 3.01 (t, J=7.0 Hz, 2H, $CH_2$—S), 2.74 (t, J=7.0 Hz, 2H, $CH_2$—COOH), 1.48 (s, 9H, 3×$CH_3$).

$^{13}$C NMR (100 MHz, $CDCl_3$): δ 178.2 (COOH), 168.9 (CO), 85.3 (Cq), 34.8 ($CH_2$), 28.3 ($CH_3$), 25.7 ($CH_2$).

IR (neat): 1710, 1370, 1245, 1205, 1125, 825 cm$^{-1}$.

HRMS-ESI: calcd. for $C_8H_{14}O_4S$: 205.0535; found: 205.0535.

Preparation of Compound 3a (Scheme 1)

EDCI (3 equiv, 5.64 mmol, 875.6 mg) and $Et_3N$ (3 equiv, 5.64 mmol, 570.7 mg) were added to a solution of 1a (1 equiv, 1.88 mmol, 2 g) and 2 (2 equiv, 3.77 mmol, 778 mg) in DCM (20 mL). The reaction mixture was stirred 24 hr at rt and subsequently washed with sat. $NH_4Cl$ solution (2×20 mL) and with sat. $NaHCO_3$ solution (2×20 mL). The organic phase was dried ($MgSO_4$), concentrated in vacuo. The product was purified by FCC on silica gel (DCM/MeOH 20:1 to 10:1) to afford 3a as a yellowish oil (1.74 mmol, 1.94 g, 93%).

$^1$H-NMR (400 MHz, $CDCl_3$): δ 6.30 (s, 1H, NH), 3.69-3.63 (m, 80H, 40×$CH_2$—O—$CH_2$), 3.60-3.54 (m, 2H, $CH_2$—O), 3.47 (t, J=5.2 Hz, 2H, $CH_2$—NH), 3.42-3.38 (m, 2H, $CH_2$—$N_3$), 3.05 (t, J=7.1 Hz, 2H, $CH_2$—CO), 2.53 (t, J=7.2 Hz, 2H, $CH_2$—S), 1.48 (s, 9H, 3×$CH_3$).

$^{13}$C NMR (100 MHz, $CDCl_3$): δ 170.8 (CO), 169.2 (CO), 84.9 (Cq), 70.7 ($CH_2$), 70.7 ($CH_2$), 70.6 ($CH_2$), 70.6 ($CH_2$), 70.2 ($CH_2$), 70.0 ($CH_2$), 69.8 ($CH_2$), 50.8 ($CH_2$), 39.3 ($CH_2$), 36.6 ($CH_2$), 28.2 (3×$CH_3$), 26.7 ($CH_2$).

IR (neat): 2860, 2110, 1700, 1670, 1545, 1465, 1345, 1290, 1250, 1205, 1110, 1030, 945, 840 cm$^{-1}$.

HRMS-ESI: calcd. for $C_{52}H_{102}N_4O_{24}SNa$: 1221.6503; found: 1221.6501.

Preparation of PEG-a I (Scheme 1)

To a solution of compound 3a (1 equiv, 1.46 mmol, 1.5 g) in toluene (7.5 mL) was added $PPh_3$ (1.8 equiv, 2.70 mmol, 708 mg) and the reaction was stirred for 30 min at rt. Then, 1M HCl (19.7 mL) was added and the reaction was stirred for 48 hr at rt. The two phases were separated and the organic phase was washed with 1 M HCl (2×20 mL). The combined aqueous layers were washed with DCM (10 mL) before being concentrated in vacuo. After co-evaporation with toluene (3×10 mL), pure compound PEG-a I was obtained as a yellowish amorphous solid (3.37 µmol, 3.32 g, 95%).

$^1$H-NMR (400 MHz, $CDCl_3$): 7.64 (s, 1H, $NH_2$), 3.78 (m, 2H, $CH_2$—$CH_2$—$NH_2$), 3.63-3.54 (m, 80H, $CH_2$—O—$CH_2$), 3.41 (m, 2H, $CH_2$—$N_3$), 3.10 (m, 2H, $CH_2$—$NH_2$), 2.78 (m, 2H, $CH_2$—SH), 2.64 (m, 2H, $CH_2$—CO), 1.68 (s, 1H, SH).

$^{13}$C NMR (100 MHz, $CDCl_3$): δ 172.3 (CO), 70.3 ($CH_2$), 70.2 ($CH_2$), 70.2 ($CH_2$), 70.1 ($CH_2$), 70.0 ($CH_2$), 69.8 ($CH_2$), 69.1 ($CH_2$), 66.7 ($CH_2$), 40.1 ($CH_2$), 39.6 ($CH_2$), 39.2 ($CH_2$), 20.7 ($CH_2$).

IR (neat): 2860, 1660, 1555, 1465, 1340, 1300, 1250, 1095, 1035, 950, 845, 730 cm$^{-1}$.

HRMS-ESI: calcd. for $C_{47}H_{96}N_2O_{22}S$: 1073.6254; found: 1073.6285.

Preparation of Compound 4 (Scheme 1)

EDCI (1.5 equiv, 72 mmol, 11.17 g) and NHS (1.5 equiv, 72 mmol, 8.36 g) were added to a solution of lipoïc acid (1 equiv, 48 mmol, 10 g) in DMF (30 mL). The reaction mixture was stirred 12 hr at rt and concentrated in vacuo. The crude product was dissolved in DCM and washed three times with $H_2O$ and brine. The organic phase was dried ($MgSO_4$) and concentrated in vacuo. The product was purified by FCC on silica gel (EtOAc/PE 1:1) to afford 4 as a yellow solid (22.42 mmol, 6.79 g, 46%).

$^1$H-NMR (400 MHz, $CDCl_3$): δ 3.65-3.49 (m, 1H, CH—S), 3.24-3.05 (m, 2H, $CH_2$—S), 2.83 (s, 4H, 2×$CH_2$—CO), 2.62 (t, J=7.3 Hz, 2H, $CH_2$—CO), 2.53-2.39 (m, 1H, H—CH—$CH_2$—S), 1.98-1.86 (m, 1H, H—CH—$CH_2$—S), 1.85-1.65 (m, 4H, $CH_2$—CH—S, $CH_2$—$CH_2$—CO), 1.63-1.49 (m, 2H, $CH_2$—$CH_2$—$CH_2$—CO).

$^{13}$C NMR (100 MHz, $CDCl_3$): δ 169.3 (2×CO), 168.5 (CO), 56.2 (CH), 40.3 ($CH_2$), 38.6 ($CH_2$), 34.5 ($CH_2$), 30.9 ($CH_2$), 28.4 ($CH_2$), 25.7 ($CH_2$), 24.5 ($CH_2$).

IR (neat): 2940, 1810, 1780, 1460, 1420, 1410, 1375, 1360, 1205, 1070, 900, 880, 810, 730 cm$^{-1}$.

HRMS-ESI: calcd. for $C_{12}H_{17}NO_4S_2Na$: 326.0497; found: 326.0497.

Preparation of Compound 5a (Scheme 1)

To a solution of compounds 1a (1 equiv, 4.72 mmol, 5 g) and 4 (2 equiv, 9.44 mmol, 2.86 g) in DMF (35 mL), $Et_3N$ (1 equiv, 4.72 mmol, 477 mg) was added. The reaction mixture was stirred for 48 hr at rt before evaporating the solvent in vacuo. The crude was dissolved in DCM (100 mL) and washed with sat. $NH_4Cl$ (2×40 mL). The organic phase was dried ($MgSO_4$) and concentrated in vacuo. The product was purified by FCC on silica gel (DCM/MeOH 17:1) to afford 5a as a yellowish amorphous solid (3.71 mmol, 4.63 g, 78%).

$^1$H-NMR (400 MHz, $CDCl_3$): δ 6.23 (s, 1H, NH), 3.70-3.58 (m, 80H, 40×$CH_2$—O—$CH_2$), 3.65-3.49 (m, 1H, CH—S), 3.56-3.51 (m, 2H, $CH_2$-0), 3.42 (q, J=5.1 Hz, 2H, $CH_2$—NH), 3.37 (t, J=4.2 Hz, 2H, $CH_2$—$N_3$), 3.23-3.04 (m, 2H, $CH_2$—S), 2.44 (m, 1H, H—CH—$CH_2$—S), 2.17 (t, J=7.5 Hz, 1H, $CH_2$—CO), 1.97-1.82 (m, 1H, H—CH—$CH_2$—S), 1.75-1.59 (m, 4H, $CH_2$—CH—S, $CH_2$—$CH_2$—CO), 1.51-1.37 (m, 1H, $CH_2$—$CH_2$—$CH_2$—CO).

$^{13}$C NMR (100 MHz, $CDCl_3$): δ 172.8 (CO), 77.4 ($CH_2$), 77.1 ($CH_2$), 76.7 ($CH_2$), 70.7 ($CH_2$), 70.6 ($CH_2$), 70.6 ($CH_2$), 70.2 ($CH_2$), 70.0 ($CH_2$), 69.9 ($CH_2$), 56.4 (CH), 50.7 ($CH_2$), 40.2 ($CH_2$), 39.2 ($CH_2$), 38.5 ($CH_2$), 36.3 ($CH_2$), 34.7 ($CH_2$), 28.9 ($CH_2$), 25.4 ($CH_2$).

IR (neat): 2870, 2100, 1635, 1555, 1465, 1345, 1280, 1250, 1105, 960, 850 cm$^{-1}$.

HRMS-ESI: calcd. for $C_{52}H_{102}N_4O_{22}S_2Na$: 1221.6324; found: 1221.6367.

Preparation of Compound PEG-a II (Scheme 1)

Compound 5a (1 equiv, 866 µmol, 1 g) was dissolved in dry THF (5 mL) under argon atm. $LiAlH_4$ (2 equiv, 1.73 mmol, 66 mg) was added portion-wise and the reaction was stirred for 40 min at rt. The reaction was quenched with addition of EtOAc (2 mL) drop-wise then $H_2O$ and the product was extracted with DCM (3×30 mL). The combined organic layers were dried ($MgSO_4$) and concentrated in vacuo to afford PEG-a II as a white amorphous solid (791 µmol, 895 g, 91%).

IR (neat): 2885, 1640, 1555, 1465, 1360, 1345, 1280, 1240, 1105, 960, 845 cm$^{-1}$.

HRMS-ESI: calcd. for $C_{52}H_{106}N_2O_{22}S_2$: 1175.6757; found: 1175.6735. calcd for: $C_{52}H_1O_4N_2O_{22}S_2Na$: 1173.6600; found: 1173.6677.

Preparation of Compound 6 (Scheme 1)

Pyridine (3 equiv, 282.6 mmol, 22.3 g, 22.8 mL) was added dropwise to a mixture of 3-mercaptopropionic acid (1 equiv, 94.2 mmol, 10 g, 8.2 mL) and acetic anhydride (3 equiv, 282.6 mmol, 28.8 g, 26.5 mL). The reaction solution was stirred for 16 hr at rt and concentrated in vacuo. The crude product was dissolved in DCM and washed three times with $KHSO_4$ 1 M. The organic phase was dried ($MgSO_4$), concentrated in vacuo and the product was purified by FCC on silica gel (DCM/MeOH 10:1) to afford the desired intermediate as a yellowish oil (53 mmol, 7.85 g, 56%). EDCI (1.5 equiv, 79.4 mmol, 15.2 g) and NHS (2 equiv, 106 mmol, 12.2 g) were added to a solution of intermediate (1 equiv, 53 mmol, 7.85 g) in DMF (50 mL). The reaction mixture was stirred 16 hr at rt and concentrated in vacuo. The crude product was dissolved in DCM and washed three times with $H_2O$ and brine. The organic phase was dried ($MgSO_4$), concentrated in vacuo. The product was purified by FCC on silica gel (EtOAc/PE 7:8) to afford the desired NHS ester as a white solid (37.3 mmol, 9.14 g, 70%). The NHS ester (1 equiv, 16.3 mmol, 4 g) was dissolved in DCM (15 mL) and $Et_3N$ (1.2 equiv, 19.6 mmol, 1.98 g, 2.73 mL) and propargylamine was added drop-wise (1 equiv, 16.3 mmol, 98 mg, 1.1 mL). The reaction solution was stirred for 16 hr at rt and the DCM layer was subsequently washed with $H_2O$ (2×20 mL), sat. $NaHCO_3$ (2×20 mL) and 0.6 M HCl (2×20 mL). The organic phase was dried ($MgSO_4$), concentrated in vacuo. The product was purified by FCC on silica gel (EtOAc/PE 1:1) to afford 6 as a white solid (10.54 mmol, 1.95 g, 63%).

$^1$H-NMR (400 MHz, $CDCl_3$): δ 6.00 (s, 1H, NH), 4.04 (dd, $^3$J=5.2, $^4$J=2.6 Hz, 2H, $CH_2$—NH), 3.12 (t, $^3$J=7.0 Hz, 2H, $CH_2$—S), 2.50 (t, $^3$J=7.0 Hz, 2H, $CH_2$—CO), 2.32 (s, 3H, $CH_3$), 2.23 (t, $^4$J=2.6 Hz, 1H, HCC).

$^{13}$C-NMR (100 MHz, $CDCl_3$): δ 196.3 (CO), 170.4 (CO), 79.5 (Cq), 71.8 (CH), 36.1 ($CH_2$), 30.7 ($CH_3$), 29.3 ($CH_2$), 24.8 ($CH_2$).

IR (neat): 3260, 3060, 2920, 1740, 1680, 1660, 1645, 1540, 1420, 1355, 1255, 1210, 1140, 1115, 965 cm$^{-1}$.

HRMS-ESI: calcd. for $C_8H_{11}NO_2SNa$: 208.0408; found: 208.0409.

Preparation of Compound 7a (Scheme 1)

Compounds 1a (1 equiv, 1.33 mmol, 1.5 g) and 6 (1.15 equiv, 1.53 mmol, 283 mg) were dissolved in a mixture of DMF:$H_2O$ 1:1 (20 mL). Catalytic amount of $CuSO_4$ (1 mg) and sodium ascorbate (1 mg) were added and the reaction mixture was stirred for 2 hr at rt. DCM (50 mL) was added and the organic phase was washed with $H_2O$ (20 mL) and 1% aqueous $NH_3$ (2×20 mL). The organic phase was dried ($MgSO_4$), concentrated in vacuo. The product was purified by FCC on silica gel (DCM/MeOH 11:1 to 4:1) to afford 7a as a yellowish oil (1.09 mmol, 1.44 g, 83%).

$^1$H-NMR (400 MHz, $CDCl_3$): δ 7.71 (s, 1H, CH), 6.53 (s, 1H, NH), 5.05 (s, 1H, NH), 4.49 (m, 4H, $CH_2$—$CH_2$—N, $CCH_2$—NH), 3.85 (m, 2H, $CH_2$—$CH_2$—N), 3.68-3.55 (m, 80H, 40×$CH_2$—O—$CH_2$), 3.51 (t, $^3$J=5.1 Hz, 2H, $CH_2$—$CH_2$—NH), 3.28 (m, 2H, $CH_2$—NH), 3.11 (t, $^3$J=7.0 Hz, 2H, $CH_2$—S), 2.48 (t, $^3$J=7.0 Hz, 2H, $CH_2$—CO), 2.29 (s, 3H, $CH_3$), 1.42 (s, 9H, 3×$CH_3$).

$^{13}$C-NMR (100 MHz, $CDCl_3$): δ 185.9 (CO), 170.7 (CO), 156.1 (CO), 144.5 (Cq), 123.4 (CH), 79.2 (Cq), 70.6 ($CH_2$), 70.3 (CH$_2$), 69.5 (CH$_2$), 50.4 (CH$_2$), 40.4 (CH$_2$), 36.0 (CH$_2$), 35.2 (CH$_2$), 30.7 (CH$_3$), 28.5 (3×CH$_3$), 24.9 (CH$_2$).

IR (neat): 3335, 2865, 1690, 1730, 1530, 1460, 1350, 1250, 1100, 950, 845 cm$^{-1}$.

HRMS-ESI: calcd. for C$_{57}$H$_{109}$N$_5$O$_{25}$SNa: 1318.7030; found: 1318.7072.

Preparation of Compound PEG-a III

4 M HCl in dioxane (13 mL) was added to compound 7a (1 equiv, 0.97 mmol, 1.3 g) and the reaction mixture was stirred for 2 hr at rt. Dioxane was removed to obtain acylated intermediate as a yellowish oil in a quantitative yield (0.97 mmol, 1.23 mg).

$^1$H-NMR (400 MHz, CDCl$_3$): δ 7.92 (s, 2H, NH$_2$), 7.77 (s, 1H CCH—N), 6.94 (s, 1H, NH), 4.48 (m, 4H, CH$_2$—CH$_2$—N, CCH$_2$—NH), 3.84 (m, 4H, CH$_2$CH$_2$—N, CH$_2$—NH$_2$), 3.73-3.51 (m, 80H CH$_2$—O—CH$_2$), 3.15 (m, 2H, CH$_2$—CH$_2$—NH$_2$), 3.09 (t, $^3$J=7.0 Hz, 2H, CH$_2$—S), 2.48 (t, $^3$J=7.0 Hz, 2H, CH$_2$—CO), 2.27 (s, 3H, CH$_3$).

$^{13}$C NMR (100 MHz, CDCl$_3$): δ 195.9 (CO), 170.9 (CO), 144.3 (Cq), 123.7 (CH), 77.4 (CH$_2$), 70.8-69.6 (CH$_2$), 69.4 (CH$_2$), 66.8 (CH$_2$), 50.5 (CH$_2$), 40.4 (CH$_2$), 40.1 (CH$_2$), 35.8 (CH$_2$), 34.9 (CH$_2$), 30.6 (CH$_3$), 24.8 (CH$_2$), 20.5 (CH$_2$).

IR (neat): 2870, 1670, 1540, 1460, 1350, 1300, 1250, 1100, 950, 845, 730 cm$^{-1}$.

HRMS-ESI: calcd. for C$_{52}$H$_{101}$N$_5$O$_{23}$S: 1196.6686; found: 1196.6713.

10% HCl solution was added to acylated intermediate (1 equiv, 836 μmol, 420 mg) and the reaction was stirred for 5 hr at 30° C. The reaction mixture was dried in vacuo to afford PEG-a III as yellowish oil (736 μmol, 850 mg, 88%).

$^1$H-NMR (400 MHz, CDCl$_3$): δ 7.92 (s, 3H, CCH—N, NH$_2$), 7.08 (s, 1H, NH), 4.54 (m, 4H, CH$_2$—N—N=N, CCH$_2$—NHCO), 3.85 (m, 4H, CH$_2$CH$_2$—N, CH$_2$—NH$_2$), 3.63-3.56 (m, 80H, CH$_2$—O—CH$_2$), 3.14 (m, 2H, CH$_2$—CH$_2$—NH$_2$), 2.75 (m, 2H, CH$_2$—SH), 2.51 (t, $^3$J=6.5 Hz, 2H, CH$_2$—CO), 1.60 (t, $^3$J=8.3 Hz, 2H, SH).

$^{13}$C NMR (100 MHz, CDCl$_3$): δ 171.1 (CO), 144.5 (Cq), 123.9 (CH), 70.8-69.6 (CH$_2$), 69.1 (CH$_2$), 66.7 (CH$_2$), 50.4 (CH$_2$), 40.1 (CH$_2$), 39.8 (CH$_2$), 34.5 (CH$_2$), 20.3 (CH$_2$).

IR (neat): 3675, 2870, 1670, 1540, 1455, 1350, 1300, 1250, 1100, 950, 845 cm$^{-1}$.

HRMS-ESI: calcd. for C$_{50}$H$_{99}$N$_5$O$_{22}$S: 1154.6581; found: 1154.6603.

Preparation of TBA-Alq (Scheme 2)

General Procedure for TBA-Alg (x)

To convert Na-alg into alginic acid, Kelton HV (2 g) was added to a mixture of aqueous HCl (30 mL, 0.6 N) and ethanol (30 mL), and the solution was stirred overnight at 4° C. The resulting solid was separated by vacuum filtration, washed with ethanol and acetone, and dried quickly under vacuum at 40° C. Dried alginic acid was dispersed in water (100 mL), and TBAOH (5 mL, 40% in water) was added. The solution was dialyzed (8× against distilled H$_2$O) and finally freeze-dried to afford TBA-alg (a) as a white solid.

General Procedure for TBA-Alg (y)

To convert Na-alg into alginic acid, Kelton HV (2 g) was dissolved in distilled H$_2$O (200 mL). 20% formic acid aqueous solution (220 mL) was added and the solution was stirred overnight at 0° C. EtOH (200 mL) was added and the resulting solid was separated by vacuum filtration, washed with H$_2$O: EtOH (1:1, 3×200 mL) and EtOH (200 mL) acetone (200 mL), and dried quickly under vacuum at 40° C. Dried alginic acid was dispersed in water (200 mL), and TBAOH (0.5 equiv, 3.4 mL, 40% in water) was added and the solution was stirred until full dispersion. The solution was directly freeze-dried without dialysis to afford TBA-alg (b) as a white solid.

Preparation of Alq-PEG Derivatives

General Protocol for the Functionalization of TBA-Alg (Scheme 2)

TBA-alg (1 equiv, 2.39 mmol, 1 g) was dissolved in DMSO (200 mL) and the solution was stirred for 12 hours to ensure high homogeneity. CDI (1 equiv, 2.39 mmol, 387 mg) previously dissolved in a minimum volume of DMSO (1 mL) was added to the solution and the reaction was stirred at room temperature (rt) for 30 min. Acetone (400 mL) was added to the reaction mixture and the resulting precipitate was filtered and washed with acetone (3×100 mL). The precipitate was transferred in a round-bottom flask and distilled water was added (100 mL). After dissolution, amino-PEG derivative (0.2 equiv, 479 μmol) dissolved in a minimum volume of water (1 mL) was added and the reaction mixture was stirred for 2 hr. The reaction was quenched by addition of a 0.05 M NaOH solution (50 mL) and the reaction mixture was directly poured into a dialysis membrane and dialyzed against distilled water. The water dialysis was changed 3 times in one day. Na-citrate solution (0.1 M, 2 mL) was added in the dialysis tube 3 times prior to the dialysis against distilled water. Then TCEP (0.1 M, 2 mL) was added in the dialysis tube 3 times prior to the dialysis against distilled water. The water dialysis was then changed 5 times before adjustment of the pH with addition of 0.05 M NaOH (30 mL) to reach pH 7. The solution was filtered (70 μm) and freeze-dried to obtain the desired product as a white solid.

Preparation of Heterobifunctional PEG Derivatives (Scheme 1)

The development of PEG-grafted alg materials for medical applications requires access to a variety of heterocheletic PEG oligomers. Following our previous reports on the production of azido- and amino-silanized PEG molecules [22, 23], straightforward synthetic pathways were developed to produce several thiol-functionalized PEG derivatives. Starting from linear PEG (HOCH$_2$(CH$_2$OCH$_2$)$_n$CH$_2$OH with average n value of 22 or 44, identified as PEG-a or PEG-b) the key intermediates α-amino-ω-azido poly (ethylene glycol) 1a and 1b, were obtained in good overall yields (3 steps) (Scheme 1). PEG I oligomers were obtained by a coupling reaction with protected 3-mercaptopropanoïc acid (2), followed by simultaneous reduction of the azido group and deprotection of the thiol functionality. Alternatively, conjugation to activated lipoic acid followed by reduction in the presence of LiAlH$_4$ delivered PEG II as mixtures of opened (reduced) and closed (oxidized) forms of the lipoyl functionality. Finally, the rigidity of the PEG chain can be decreased by introduction of a triazole moiety using a click reaction catalyzed by copper species to produce PEG III.

Scheme 1. Preparation of heterobifunctional PEG derivatives for functionalization of alginate

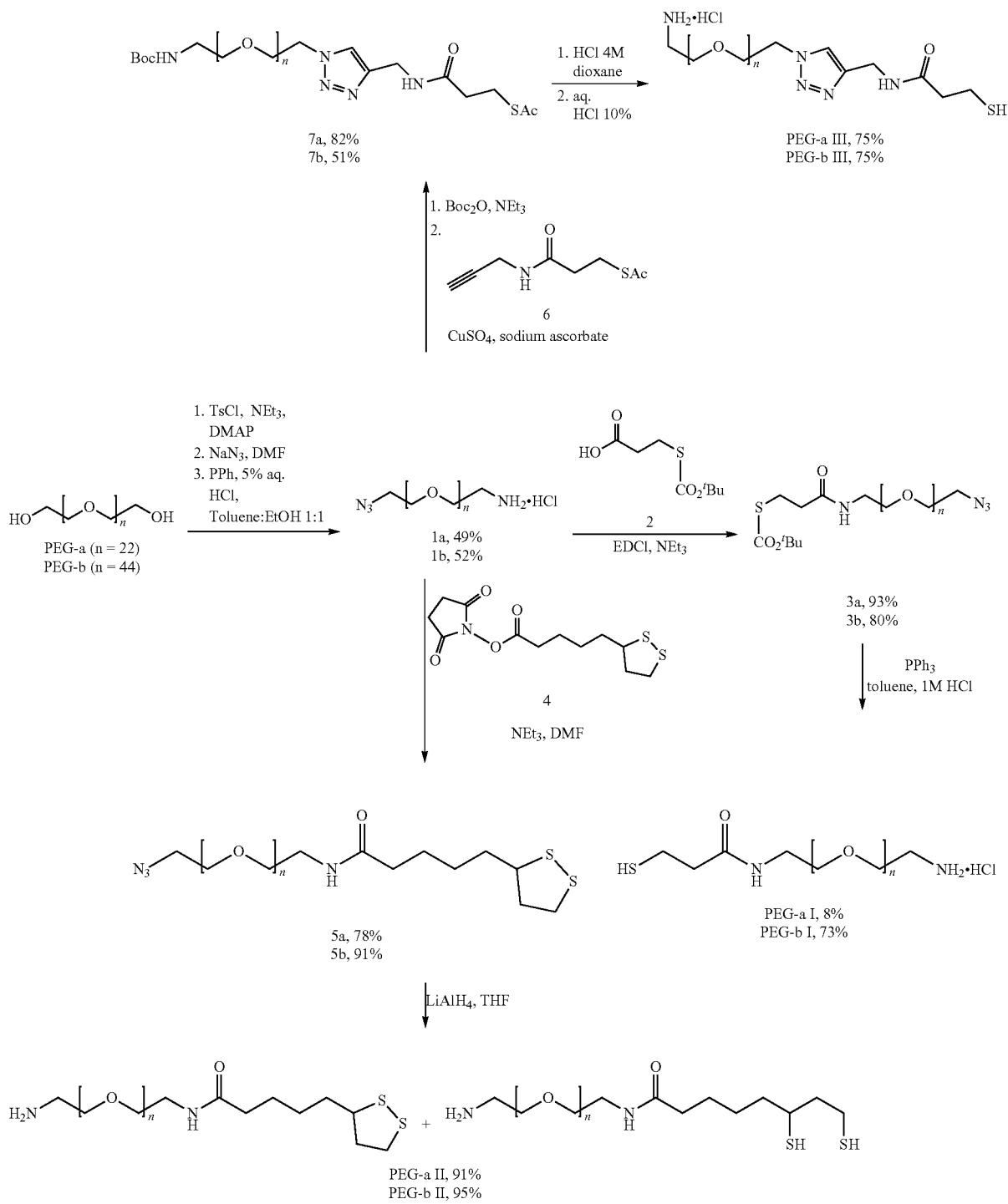

Functionalization of Na-Alg with PEG Derivatives (Scheme 2)

In order to maintain all carboxyl groups of Na-alg available for ionic cross-linking, we focused on the modification of hydroxyl groups. Na-alg (Kelton HV) was first converted into TBA-alg to increase solubility in DMSO for further chemical derivatization (Scheme 2). Heterogeneous acidification of Na-alg was performed either in aqueous ethanolic HCl or aqueous formic acid, [24] followed by treatment with TBAOH to afford TBA-alg polymers (TBA-alg(x); TBA-alg(y)). Activation of hydroxyl groups in the presence of carbodiimidazole for 0.5 h and subsequent precipitation provided the activated imidazolide. Condensation with PEG derivatives I-III followed by purification through dialysis and freeze drying afforded PEG-grafted Na-alg for MS formation.

Scheme 2. Functionalization of Na-alg with PEG derivatives

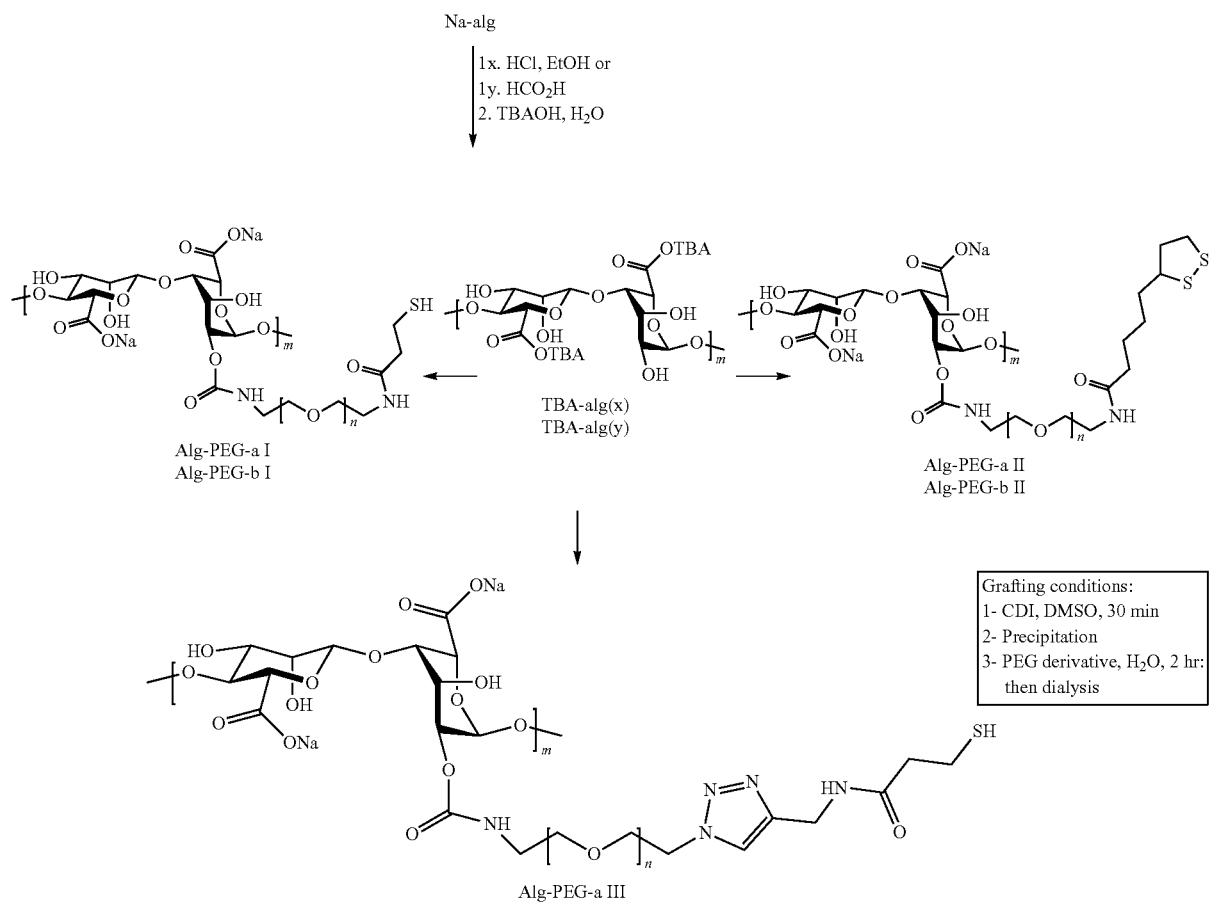

The chemical structures of intermediate TBA-alg and PEG grafted alginates were confirmed by NMR analysis. The viscosity of solutions containing various concentrations of the polymers was measured to optimize the conditions for MS formation (Table 1).

TABLE 1

Properties of intermediate TBA-alg and PEG grafted alginates

| Product | Ratio TBA/Alg[1] | % grafting[2] (mol %) | Viscosity (mPa · s) | Formulation No |
|---|---|---|---|---|
| TBA-alg(x) | 2.01 | — | 133.1 (2 wt %) | |
| TBA-alg(y) | 2.35 | — | 195.3 (2 wt %) | |
| Alg-PEG-a I(x) | — | 5.9 | 209.0 (3 wt %) | 1 |
| Alg-PEG-a I(y) | — | 4.05 | — | |
| Alg-PEG-b I(x) | — | 13 | 53.4 (4 wt %) | 2 |
| Alg-PEG-a II(x) | — | 7.6 | 160.7 (3 wt %) | 3 |
| Alg-PEG-b II(x) | — | 21 | 160.9 (4 wt %) | 4 |
| Alg-PEG-a III(x) | — | 9.4 | 179.7 (3 wt %) | 5 |

[1]Determined by $^1$H-NMR;
[2]Determined by $^1$H-NMR;
x: initial treatment of Na-alg with ethanolic HCl;
y: initial treatment of Na-alg with formic acid.

3. Microsphere Formation from PEG Grafted Alginate Derivatives

Solutions of Alg-PEG, at the concentrations indicated in Table 1, were extruded into a gelation bath containing $CaCl_2$) as ionic cross-linker to produce one-component MS which were assessed for their size, mechanical resistance to compression, elasticity and permeability.

3.1 Size and Morphology

Size and morphology of the MS are reported in Tables 2 and 3.

TABLE 2

Size and morphology of MS

| Product[1] | Formulation No | | | | |
|---|---|---|---|---|---|
| | 1 Alg-PEG a I | 2 Alg-PEG b I | 3 Alg-PEG a II | 4 Alg-PEG b II | 5 Alg-PEG-a III |
| Diameter at day 1 (μm)[2] | 934.00 ± 100.81 | 1335.90 ± 118.27 | 667.23 ± 98.44 | 759.70 ± 82.85 | 454.80 ± 44.32 |
| Diameter at day 7 (μm)[2] | 913.07 ± 105.56 | 1263.33 ± 121.72 | 642.13 ± 84.52 | 715.40 ± 75.72 | 452.80 ± 42.55 |

[1]Grafting with PEG derivatives was performed on TBA-alg(x);
[2]MS were kept in MOPS at 25° C. (10 mM, pH = 7.4);
[3]Olympus AX70 microscope equipped with an Olympus DP70 color digital camera For each PEG derivative, an increase of the length of the grafted chain resulted in an increase of the diameter of the beads (formulations 1 vs 2; 3 vs 4). Evaluation of the MS diameters, after beads formation (day 1) and after one week (day 7), did not show significant changes of the MS. In comparison, Na-Alg MS show a diameter of 997±127 μm$^2$ at day 1 and of 986±81 μm$^2$ at day 7.

TABLE 3

Size and morphology of MS from Alg-PEG-a I prepared from TBA-alg(y)

| Product | Diameter at day 3 (μm)[2] | Diameter at day 7 (μm)[2] |
|---|---|---|
| Alg-PEG-a I[1] | 757.53 ± 73.47 | 737.8 ± 79.03 |

[1]Grafting with PEG derivatives was performed on TBA-alg(y);
[2]MS were kept in MOPS at 25° C. (10 mM, pH = 7.4);
[3]Olympus AX70 microscope equipped with an Olympus DP70 color digital camera The MS were then evaluated for their mechanical resistance to compression and permeability.

3.2 Mechanical Resistance to Compression

Mechanical resistance to uniaxial compression was measured after completion of covalent cross-linking. Upon compression of 40-50% of their initial diameter, all MS showed minimal mechanical resistance. An increase of mechanical resistance was observed from 70% and the resistance became exponential until 90% compression. FIG. 1 presents the mechanical resistance to 90% compression of one-component MS listed in Tables 2 and 3.

The mechanical properties of the MS were further assessed by evaluation of shape recovery performance upon repeated compression at 90% of the initial MS diameter (FIG. 2). One of the shortcomings of the physical properties of Ca-alg MS is their poor elasticity. MS formed by Alg-PEG I and Alg-PEG II showed a good recovery performance.

3.3 Permeability Assessment

Figure 3:
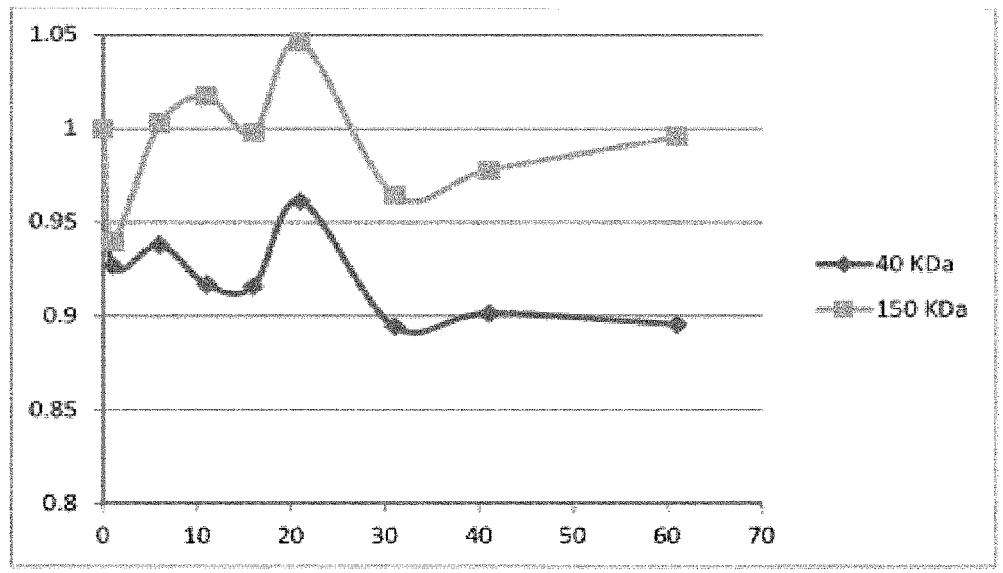
FIG. 3. Permselectivity of Alg-PEG-a I (x) MS, assessed by ingress diffusion of 40 kDa and 150 kDa FITC-dextran. Fluorescence of the supernatant.

For the permeability assessment, a MWCO of 150 kg mol$^{-1}$ is the threshold above which MS intended for cell microencapsulation and further transplantation should exclude any compound. This assessment was performed by ingress diffusion of FITC-dextran standards at 40 kg mol$^{-1}$ and 150 kg mol-1. Interestingly, all MS formed by PEG grafted alginate derivatives allowed diffusion of 40 kg mol$^{-1}$ FITC-dextran but excluded 150 kg mol$^{-1}$ FITC-dextran, indicating that their MWCO is suitable for cell microencapsulation application. This permselectivity requirement is hardly achieved by Ca-alg MS. FIG. 3 gives a representative example of the assessment of permeability by ingress diffusion of FITC-dextrans for system Alg-PEG-a I.

3.4 Stability of MS at 4 Weeks

Thus, Alg-PEG I hydrogels with degree of grafting of 15 to 20% produce microspheres which are stable for more than 4 weeks in 25 mM sodium citrate solution. Under the same conditions, Ca-Alg microspheres dissolve within 48 hours. These results highlight the importance of covalent cross-linking to reinforce the stability of the microsphere network.

4. Evaluation of PEG Grafted Alginate-Based Hydrogels for Cell Microencapsulation Cell Viability of MS Encapsulation of MIN6 cells by both Alg-PEG-a I or Alg-PEG-a II was performed under physiological conditions by extrusion in a gelation bath containing CaCl$_2$). This one-step process delivered MS of average diameters between 500 and 600 μm. Cell viability was assessed by FDA/PI staining (FIG. 4A).

Homogeneous cells distribution within both MS types was observed and no free cells were detected in the surrounding medium.

The cell viability was measured at day 3, day 10 and day 15 (FIG. 4B). Cell viability was confirmed over 15 days after microencapsulation. The integrity of the MS from Alg-PEG a I system was confirmed as no free cells were identified in the culture medium. The integrity of the MS from Alg-PEG-a II system degraded over time and out-diffusion of the cells was observed around day 10. In light microscopy the microspheres showed a lucent appearance. Stability of the MS can thus be tuned by the chemical composition of the PEG-Alg hydrogel.

This observation indicates that covalent cross-linking resulting from 1,2-dithiolane moieties is reversible under the physiological conditions used for cell culture. Changing the functionalities installed on the PEG chain for covalent cross-linking seems to have the potential to modulate the stability of the resulting MS so that the functionalization of the alginate derivative can be selected depending on the type of intended application.

Due to the combination of electrostatic interactions with divalent cations and covalent crosslinking (disulfide bridges and disulfide clusters), the in vitro and in vivo durability of Alg-PEG hydrogels can be tuned depending on the targeted application.

5. Glucose-Stimulated Insulin Release Assay

Figure 5:
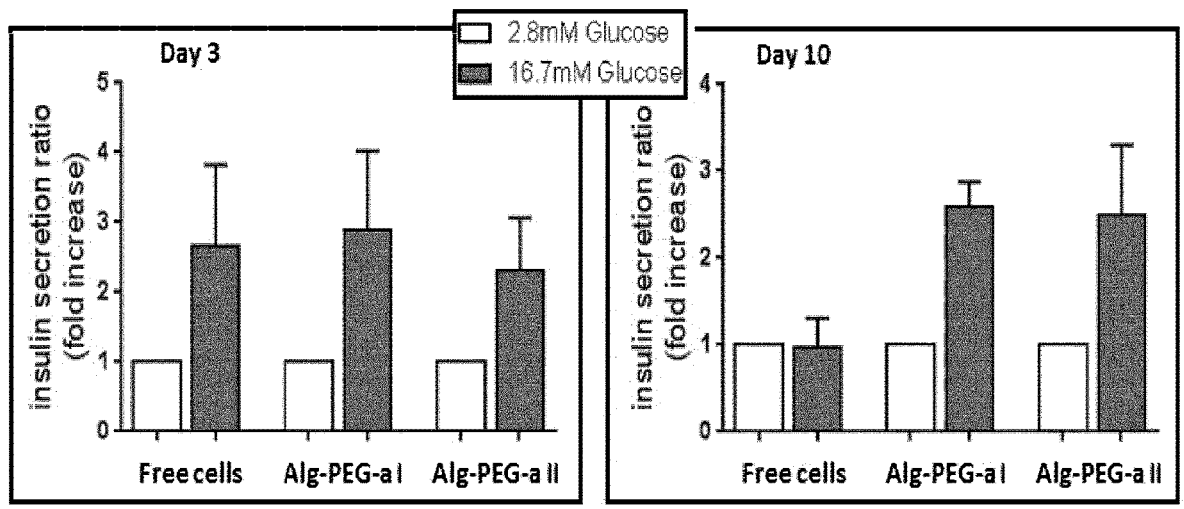
FIG. 5. Glucose-stimulated insulin release for non-encapsulated MIN6 cells and MIN6 cells microencapsulated in MS from Alg-PEG-a I and Alg-PEG-a II.

Free non-encapsulated MIN6 cells and microencapsulated MIN6 cells were subjected to a glucose-stimulated insulin release assay under static conditions, for both MS at day 3 and day 6 after microencapsulation. Stimulation was done at a glucose concentration of 16.7M, and the fold increase in insulin concentration was calculated with respect to glucose at basal concentration of 2.8M, with correction for the total level of insulin during the culture (FIG. 5). The assay outcome was the same for free MIN6 cells and microencapsulated MIN6 cells, using either Alg-PEG-a I or Alg-PEG-a II MS types. The functionalized alginate based hydrogels are thus suitable for maintaining insulin-secreting capacity of microencapsulated cells.

6. Microencapsulation of Primary Porcine Hepatocytes

Figure 6:
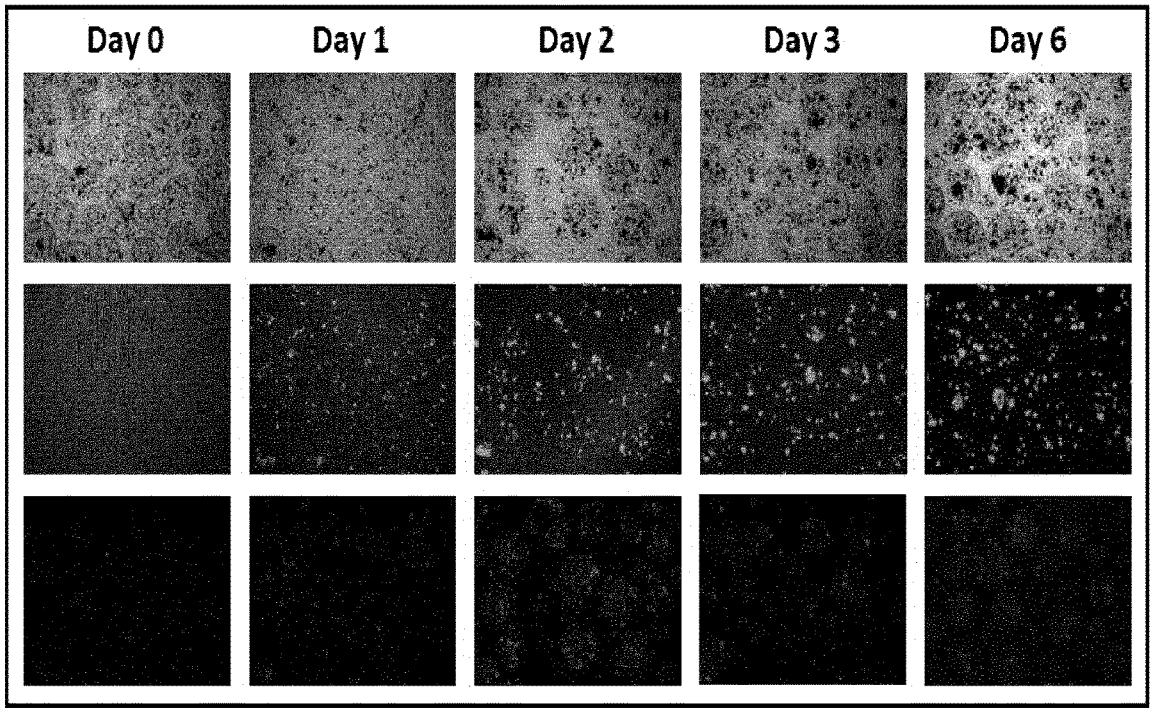
FIG. 6. Primary porcine hepatocytes microencapsulated in MS from Alg-PEG-a I (microsphere diameter about 500 µm): photographs are from the day of microencapsulation till day 6 after subsequent culture. Upper panels, light microscopy; middle panel, staining of live cells with fluorescein diacetate; lower panel, staining of dead cells with propidium iodide.

The Alg-PEG-a I system was further evaluated for the microencapsulation of primary porcine hepatocytes. Hepatocytes were isolated from pigs of 10 kg. The microencapsulated primary hepatocytes remained viable for a culture period up to 10 days (FIG. 6). This is illustrated in FIG. 6 for a culture until 6 days.

Figure 7:
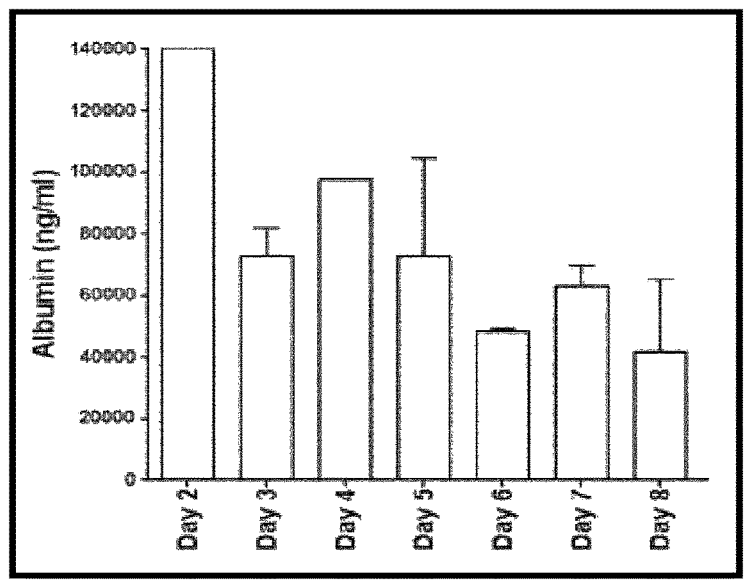
FIG. 7. Albumin synthesis of primary porcine hepatocyte in MS from Alg-PEG-a I. The daily synthesis was assessed upon daily exchange of the medium.

The production of albumin by microencapsulated hepatocytes was measured daily, with daily exchange of the medium (FIG. 7). The capacity for albumin secretion is maintained upon microencapsulation, with a tendency to decrease in time.

7. Transplantation of MS in Immune-Competent Mice

The compatibility of Alg-PEG-a I and Alg-PEG-a II for cell transplantation was assessed by the transplantation of empty MS formed from both systems in immune-competent mice, with a follow-up period of 30 days. Then, the MS were macroscopically inspected and retrieved (FIG. 8). At macroscopic inspection, MS were visible. There were no signs of inflammation, connective tissue formation nor fibrosis, indicating host compatibility for MS with Alg-PEG-a I or Alg-PEG-a II.

8. Active Principles—Bioactive Agents

The production of PEG-grafted alginate offers the opportunity for further functionalization of the resulting hydrogel with active principle and/or bioactive agents to improve the biocompatibility of the microspheres for cell transplantation. Poly(ethylene glycol) derivatives functionalized were produced with the anti-inflammatory active principle ketoprofen (KT), using either an ester or an amide linkage so that the in vivo release kinetics can be tuned by the nature of the covalent bond (Scheme 3).

These derivatives were further used for the functionalization of alginate according to the grafting procedure described herewith in the synthesis part and on scheme 4. The grafting was probed by DOSY NMR experiments which gave evidence for the covalent conjugation to ketoprofen-functionalized PEG derivatives.

These alginate derivatives were further processed to produce microspheres and the following aspects were highlighted:

(1) Both Alg-PEG-ester-KT and Alg-PEG-amide-KT polymers can be used for the microencapsulation of insulin producing cells (MIN6 cells were used as model)

(2) The release of ketoprofen from Alg-PEG-ester-KT microspheres could be observed, in vitro, over 2 weeks.

In addition, microspheres were produced from a mixture of Alg-PEG-ester-KT and Alg-PEG I polymers to produce spherical matrices presenting: i) electrostatic interactions; ii) covalent disulfide bond linkages; iii) surface ketoprofen functionalization (Scheme 5).

These experiments demonstrate the versatility of the synthetic methods herein presented, providing access to hybrid electrostatic-covalent microspheres further functionalized with active principle and/or bioactive agents to reduce inflammation and fibrosis after transplantation.

Experimental Results

Na-alg was grafted with a PEG previously conjugated to ketoprofen through either amide or ester linkage (schemes 3 and 4). MS were formed from a mixture of Na-alg and these functionalized alginate derivatives. The MS functionalized with ketoprofen were stable for 14 days at 37° C. in DMEM supplemented with FCS and antibiotics (streptomycin/penicillin). The release of ketoprofen from the MS was quantified by LC-MS at pH 3, pH 7.4 and pH 11 (FIG. 9). The curves shows controlled release of ketoprofen over time depending on the pH of the medium. A fast release is observed at basic pH as hydrolysis of ester is a fast process under basic conditions. Large quantities of active principle and/or active agent is released following MS formation.

At physiological pH (7.4), the kinetic is slower and allows small amounts of active principle and/or active agents to diffuse out of the MS over a long period. At acidic pH, the release is even slower. This is in agreement with the nature of the chemical bond (ester) to the active agent.

Thus, insulin producing cells MIN6 are viable and produce insulin once encapsulated in these systems (control performed at day 7).

Scheme 3. Preparation of PEG-ketoprofen conjugates

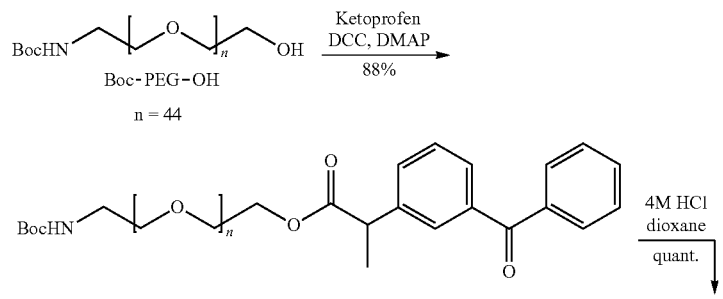

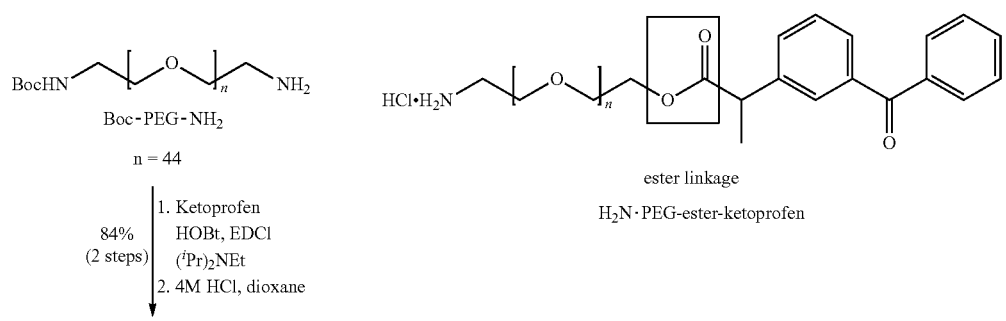
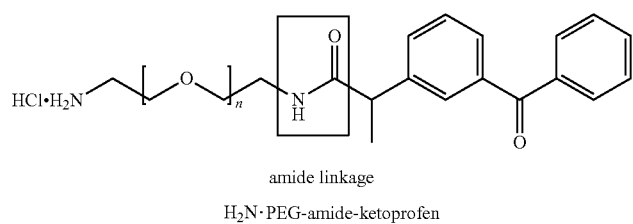
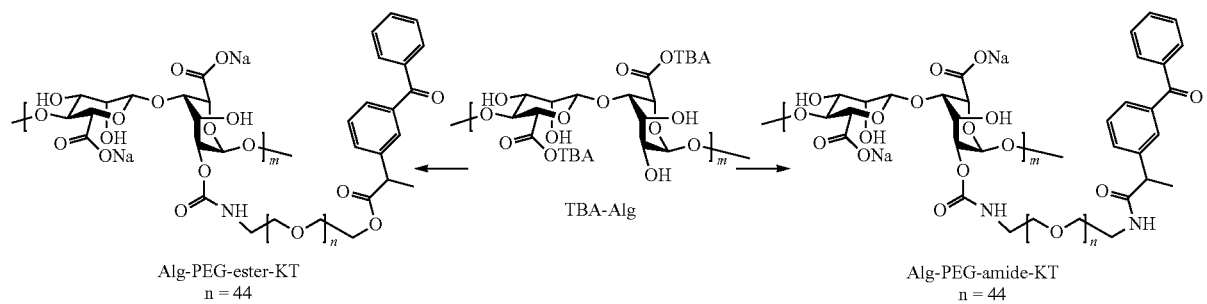
Scheme 4. Functionalization of alginate with anti-inflammatory agent
Conditions
1 CDI, DMSO, 1.5 h
2 precipitation
2 H₂N·PEG-ester-ketoprofen
or H₂N·PEG-amide-ketoprofen
H₂O, 2 h Scheme 5. Preparation of hybrid functionalized microspheres

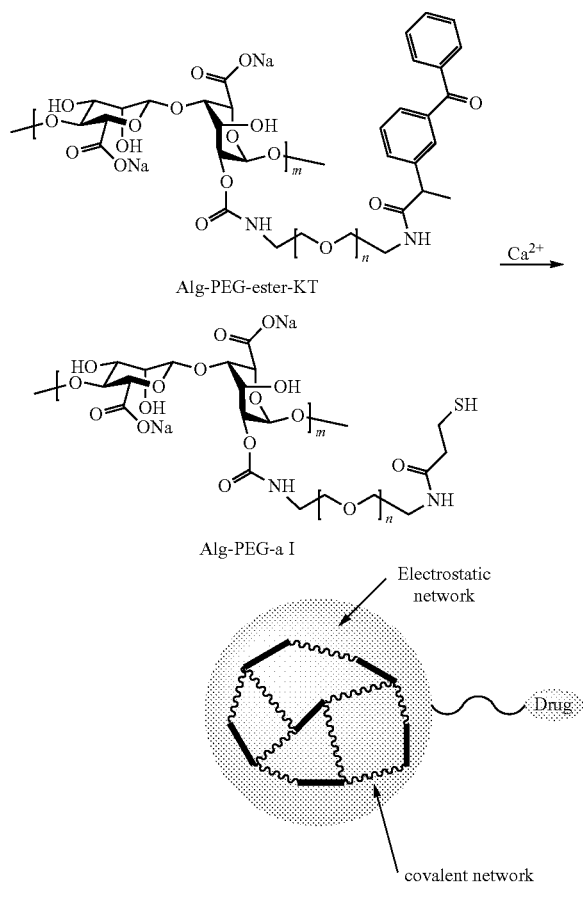

REFERENCES

1. Lee, K. Y.; Mooney, D. J. Alginate: Properties and biomedical applications. *Prog. Polym. Sci.* 2012, 37, 106-126.
2. Goh, C. H.; Heng, P. W. S.; Chan, L. W. Alginates as a useful natural polymer for microencapsulation and therapeutic applications. *Carbohydr. Polym.* 2012, 88, 1-12.
3. Nedovic, V.; Willaert, R. Applications of Cell Immobilization Biotechnology; Springer: Dordrecht, 2005.
4. O'Sullivan, E. S.; Vegas, A.; Anderson, D. G.; Weir, G. C. Islets transplanted in immunoisolation devices: A review of the progress and the challenges that remain. *Endocr. Rev.* 2011, 32, 827-844.
5. Basta, G.; Calafiore, R. Immunoisolation of pancreatic islet grafts with no recipient's immunosuppression: Actual and future perspectives. *Curr. Diabetes Rep.* 2011, 11, 384-391.
6. Drury, J. L.; Dennis, R. G.; Mooney, D. J. The tensile properties of alginate hydrogels. *Biomaterials* 2004, 25, 3187-3199.
7. Moya, M. L.; Morley, M.; Khanna, O.; Opara, E. C.; Brey, E. M. Stability of alginate microbead properties in vitro. *J. Mater. Sci.: Mater. Med.* 2012, 23, 903-912.
8. King, A.; Strand, B.; Rokstad, A. M.; Kulseng, B.; Andersson, A.; Skjåk-Braek, G.; Sandler, S. Improvement of the biocompatibility of alginate/poly-L-lysine/alginate microcapsules by the use of epimerized alginate as a coating. *J. Biomed. Mater. Res.*, Part A 2003, 64, 533-539.
9. Chen, A. Z.; Bai, Y.; Wang, S. B.; Liu, Y. G.; Chen, Z. X. Molecular biocompatibility evaluation of poly-L-ornithine-coated alginate microcapsules by investigating mRNA expression of proinflammatory cytokines. *J. Biomimetics Biomater. Tissue Eng.* 2012, 14, 53-64.
10. Wandrey, C.; Espinosa, D.; Rehor, A.; Hunkeler, D. Influence of alginate characteristics on the properties of multi-component microcapsules. *J. Microencapsulation* 2003, 20, 597-611.
11. Hu, X.; Li, D.; Gao, C. Chemically crosslinked chitosan hydrogel loaded with gelatin for chondrocyte encapsulation. *Biotechnol. J.* 2011, 6, 1388-1396.
12. Fu, Y.; Xu, K.; Zheng, X.; Giacomin, A. J.; Mix, A. W.; Kao, W. J. 3D cell entrapment in crosslinked thiolated gelatin-poly(ethylene glycol) diacrylate hydrogels. *Biomaterials* 2012, 33, 48-58.
13. Brunsen, A.; Ritz, U.; Mateescu, A.; Höfer, I.; Frank, P.; Menges, B.; Hofmann, A.; Rommens, P. M.; Knoll, W.; Jonas, U. Photocrosslinkable dextran hydrogel films as substrates for osteoblast and endothelial cell growth. *J. Mater. Chem.* 2012, 22, 19590-19604.
14. Bian, L.; Hou, C.; Tous, E. The influence of hyaluronic acid hydrogel crosslinking density and macromolecular diffusivity on human MSC chondrogenesis and hypertrophy. *Biomaterials* 2013, 34, 413-421.
15. Rockstad, A. M.; Brekke, O. L.; Steinkjer, B.; Ryan, L.; Kolláriková, G.; Strand, B. L.; Skjåk-Braek, G.; Lambris, J. D.; Lacík, I.; Mollnes, T. E.; Espevik, T. The induction of cytokines by polycation containing microspheres by a complement dependent mechanism. *Biomaterials* 2013, 34, 621-630.
16. Vériter, S.; Mergen, J.; Goebbels, R.-M.; Aouassar, N.; Grégoire, C.; Jordan, B.; Levêque, P.; Gallez, B.; Gianello, P.; Dufrane, D. in vivo selection of biocompatible alginates for islet encapsulation and subcutaneous transplantation. *Tissue Eng.: Part A*, 2010, 16, 1503-1513.
17. Dang, T. T.; Thai, A. V.; Cohen, J.; Slosberg, J. E.; Siniakowicz, K.; Doloff, J. C.; Ma, M.; Hollister-Lock, J.; Tang, K. M.; Gu, Z.; Cheng, H.; Weir, G. C.; Langer, R.; Anderson, D. G. Enhanced function of immuno-isolated islets in diabetes therapy by co-encapsulation with an anti-inflammatory drug. *Biomaterials* 2013, 34, 5792-5801.
18. Mahou, R.; Wandrey, C. Alginate-poly(ethylene glycol) hybrid microspheres with adjustable physical properties. *Macromolecules* 2010, 43, 1371-1378.
19. Mahou, R.; Kolláriková, G.; Gonelle-Gispert, C.; Meier, R. P. H.; Schmitt, F.; Tran, N. M.; Dufresne, M.; Altimar, I.; Lacík, I.; Bühler, L.; Juillerat-Jeanneret, L; Legallais, C.; Wandrey, C. Combined electrostatic and covalent polymer network for cell microencapsulation. *Macromol. Symp.* 2013, 329, 49-57.
20. Mahou, R.; Kolláriková, G.; Gonelle-Gispert, C.; Meier, R. P. H.; Schmitt, F.; Tran, N. M.; Dufresne, M.; Altimar, I.; Lacík, I.; Buhler, L.; Juillerat-Jeanneret, L; Legallais, C.; Wandrey, C. Combined electrostatic and covalent polymer network for cell microencapsulation. *Macromol. Symp.* 2013, 329, 49-57.
21. Mahou, R.; Borcard, F.; Crivelli, V.; Montanari, E.; Passemard, S.; Noverraz, F.; Gerber-Lemaire, S.; Bühler, L.; Wandrey, C. Tuning the Properties of Hydrogel Microspheres by Adding Chemical Crosslinking Functionality to Sodium Alginate. *Chem. Mater.* 2015, 27, 4380-4389.
22. Mahou, R.; Wandrey, C. Versatile Route to Synthesize Heterobifunctional Poly(ethylene glycol) of Variable Functionality for Subsequent Pegylation. *Polymers* 2012, 4, 561-589.

23. Passemard, S.; Staedler, D.; Učňová, L.; Schneiter, G. S.; Kong, P.; Bonacina, L.; Juillerat-Jeanneret, L.; Gerber-Lemaire, S. Convenient synthesis of bifunctional azido and amino-silanized poly(ethylene glycol) suitable for the functionalization of iron oxide nanoparticles for biomedical applications. *Bioorg. Med. Chem. Lett.* 2013, 23, 5006-5010.

24. Schleeh, T.; Madau, M.; Roessner, D. Synthesis enhancements for generating highly soluble tetrabutylammonium alginates in organic solvents. *Carbohydr. Polym.* 2014, 114, 493-499.

25. Mironi-Harpaz, I.; Wang, D. Y.; Venkatraman, S.; Seliktar, D. Photopolymerization of cell-encapsulating hydrogels: crosslinking efficiency versus cytotoxicity. *Acta Biomater.* 2012, 8, 1838-1848.

The invention claimed is:

1. A composition comprising:
   a. a functionalized hydrogel based on an anionic polysaccharide grafted with at least one moiety, wherein the moiety is a synthetic biocompatible polymer grafted on at least one hydroxyl group of said anionic polysaccharide;
   b. a second component selected from cells, proteins, nucleic acids, and other molecules; and
   c. an active principle or bioactive agent,
   wherein said functionalized hydrogel is in the form of a microsphere,
   wherein said second component is encapsulated within the functionalized hydrogel microsphere,
   wherein the active principle or bioactive agent is linked to the microsphere through non-covalent or covalent interactions,
   wherein the synthetic biocompatible polymer is a polyethylene glycol (PEG) or PEG derivative or a polyethyleneimine, and
   wherein the moiety is grafted on hydroxyl groups of said anionic polysaccharide through a carbamate bond.

2. The composition of claim 1, wherein the anionic polysaccharide comprises one or more carboxylic acid functional groups.

3. The composition of claim 1, wherein the anionic polysaccharide is selected from the group consisting of alginate, hyaluronan, galacturonan, and a salt thereof.

4. The composition of claim 1, wherein the degree of grafting of the moiety on hydroxyl groups of said anionic polysaccharide is comprised between 5 and 30 mol %.

5. The composition of claim 1, wherein the PEG or PEG derivative is selected from the group consisting of a linear PEG, a derivative of linear PEG, a multi-arm PEG, a derivative of multi-arm PEG, and a derivative of a linear or multi-arm PEG presenting terminal reactive functionalities.

6. The composition of claim 5, wherein the PEG, or a derivative thereof, is a heterobifunctional PEG of formula I, II and/or III:

Formula I
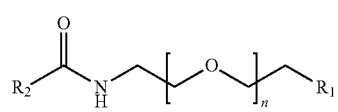

Formula II
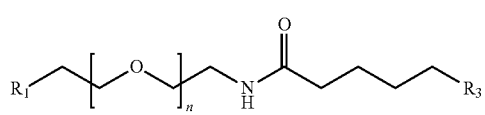

Formula III
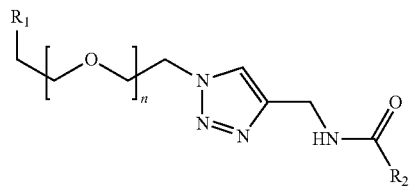

wherein, n=8 to 50;

$R_1$ is independently selected from $NH_2$, $N_3$, $OH$, and $C_{1-6}$ alkyl-$CO_2H$;

$R_2$ is independently selected from $(CH_2)_p SH$, with p=2 to 10,

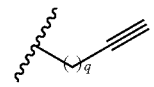 [SMILES: *CC#C]

with q=2 to 5, and

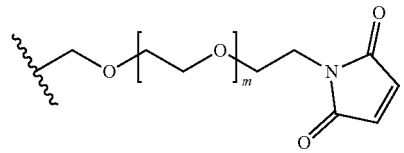

with m=2 to 10; and $R_3$ is independently selected from

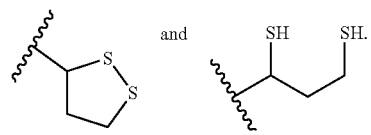 [SMILES: *C1CCSS1 ; *C(S)CCS]

7. The composition of claim 1, wherein the functionalized hydrogel is selected from Alg-PEG-a I and Alg-PEG-a II.

8. The composition of claim 1, wherein the second component is a cell from human or animal origin selected from keratinocytes, fibroblasts, osteocytes, chondrocytes, urocytes, stem cells, endothelial cells, pancreatic cells, liver cells, and neural cells.

9. The composition of claim 1, wherein the active principle or bioactive agent is an anti-inflammatory agent.

10. The composition of claim 9, wherein the anti-inflammatory agent is selected from curcumin and ketoprofen.

11. The composition of claim 1, wherein the synthetic biocompatible polymer is functionalized with the active principle or bioactive agent.

12. The composition of claim 5, wherein the functionalized hydrogel is a PEG or a PEG derivative-grafted alginate, wherein the PEG or PEG derivative is further functionalized with the active principle or bioactive agent.

13. The composition of claim 12, wherein the PEG or PEG derivative is functionalized with the active principle or bioactive agent using an ester, an amide or a hydrazine linkage or a disulfide bridge.

14. The composition of claim 13, wherein the functionalized hydrogel is alginate grafted with PEG, wherein PEG is further functionalized with ketoprofen using an ester or an amide linkage.

15. A pharmaceutical composition comprising the composition of claim 1 and a pharmaceutically acceptable carrier.

16. A method of treating and/or preventing a disease or disorder in a human or animal patient, the method comprising implanting or transplanting into a human or animal patient the composition according to claim 1.

17. The method according to claim 16, wherein the composition is implanted or transplanted as a coating for organs or for biomedical articles.

18. The method according to claim 16, wherein the composition serves as a carrier for the controlled delivery of the second component after transplantation.

19. A biomedical article coated with the composition according to claim 1.

20. A method of treating and/or preventing a disease or disorder in a human or animal patient, the method comprising administering the pharmaceutical composition according to claim 15.

* * * * *